United States Patent
Ramer et al.

(10) Patent No.: US 10,682,069 B2
(45) Date of Patent: **\*Jun. 16, 2020**

(54) USER PREFERENCE AND USER HIERARCHY IN AN ELECTROENCEPHALOGRAPHY BASED CONTROL SYSTEM

(71) Applicant: ABL IP HOLDING LLC, Conyers, GA (US)

(72) Inventors: David P. Ramer, Reston, VA (US); Jack C. Rains, Jr., Sarasota, FL (US); Youssef F. Baker, Arlington, VA (US); Niels G. Eegholm, Columbia, MD (US); Daniel M. Megginson, Fairfax, VA (US); Jenish S. Kastee, South Riding, VA (US)

(73) Assignee: ABL IP HOLDING LLC, Conyers, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/981,446

(22) Filed: May 16, 2018

(65) Prior Publication Data

US 2019/0290157 A1    Sep. 26, 2019

Related U.S. Application Data

(63) Continuation-in-part of application No. 15/934,083, filed on Mar. 23, 2018, now Pat. No. 10,551,921, and (Continued)

(51) Int. Cl.
*A61B 5/0478* (2006.01)
*G16H 40/63* (2018.01)
*A61B 5/00* (2006.01)

(52) U.S. Cl.
CPC ........ *A61B 5/0478* (2013.01); *A61B 5/6814* (2013.01); *G16H 40/63* (2018.01)

(58) Field of Classification Search
None
See application file for complete search history.

(56) References Cited

U.S. PATENT DOCUMENTS 6,473,639 B1 * 10/2002 Fischell .............. A61B 5/0476
                                                    600/544
8,457,705 B2 *  6/2013 Shoureshi .......... A61B 5/0059
                                                    600/323

(Continued)

OTHER PUBLICATIONS

"Nissan's 'B2V' system lets you drive a car with brain waves", https://www.nbcnews.com/mach/science/nissan-paves-way-cars-read-your-mind-ncna834811, searched Jan. 9, 2018 (4 pages).

(Continued)

*Primary Examiner* — Ramesh B Patel
(74) *Attorney, Agent, or Firm* — RatnerPrestia

(57) ABSTRACT

A system including an electroencephalography (EEG) device configured to be positioned on a head of a user. The system also includes a processor in communication with the EEG device, a memory accessible by the processor and instructions stored in the memory for execution by the processor to, in configuration phase, for each respective location among a plurality of locations at a respective time among a plurality of times, obtain an identification (ID) associated with the respective premises at the respective time, determine a control instruction associated with the EEG signals detected from among a plurality of control instructions; store the determined control instruction in association with the obtained premises ID, as a user preference data relative to the respective location; and at a later time, during an operational phase at the respective location, utilize the stored user preference data to communicate a (Continued)

control data signal corresponding to the determined control instruction to a controllable device at the respective premises.

17 Claims, 23 Drawing Sheets

Related U.S. Application Data a continuation-in-part of application No. 15/948,448, filed on Apr. 9, 2018, which is a continuation-in-part of application No. 15/934,083, filed on Mar. 23, 2018, now Pat. No. 10,551,921.

(56) References Cited

U.S. PATENT DOCUMENTS

| | | | | |
|---|---|---|---|---|
| 9,449,446 | B1* | 9/2016 | Mullin | G07C 9/00158 |
| 10,029,067 | B2* | 7/2018 | Gerdes | A61B 5/7415 |
| 10,223,633 | B2* | 3/2019 | Breuer | G06N 3/02 |
| 2014/0257073 | A1* | 9/2014 | Machon | A61B 5/6803 600/383 |
| 2014/0354534 | A1* | 12/2014 | Mullins | G06F 3/015 345/156 |
| 2015/0282760 | A1* | 10/2015 | Badower | A61B 5/04012 600/383 |
| 2016/0103487 | A1* | 4/2016 | Crawford | G06F 3/015 600/544 |
| 2016/0143554 | A1* | 5/2016 | Lim | A61B 5/6814 600/383 |
| 2016/0198971 | A1* | 7/2016 | Adachi | G06F 19/325 600/379 |
| 2016/0360970 | A1* | 12/2016 | Tzvieli | G01J 5/0265 |
| 2017/0172497 | A1* | 6/2017 | Marquez Chin | G06F 19/3481 |
| 2017/0199569 | A1* | 7/2017 | Cruz-Hernandez | G06F 3/016 |
| 2017/0228512 | A1* | 8/2017 | Driscoll | G06F 19/3418 |
| 2018/0092557 | A1* | 4/2018 | Bickford | A61B 5/0059 |
| 2018/0184974 | A1* | 7/2018 | Cimenser | A61B 5/04845 |
| 2018/0285540 | A1* | 10/2018 | Chen | G06F 21/32 |
| 2018/0317848 | A1* | 11/2018 | Gunasekar | A61B 5/6843 |
| 2018/0368722 | A1* | 12/2018 | Lunner | A61B 5/6803 |
| 2019/0121431 | A1* | 4/2019 | Lee | G06F 3/011 |
| 2019/0122475 | A1* | 4/2019 | Dyne | G07C 9/02 |
| 2019/0159675 | A1* | 5/2019 | Sengupta | A61B 5/0476 |
| 2019/0290157 | A1 | 9/2019 | Ramer et al. | |
| 2019/0290211 | A1* | 9/2019 | Ramer | A61B 5/7221 |
| 2019/0294244 | A1* | 9/2019 | Ramer | A61B 5/0478 |
| 2019/0294245 | A1* | 9/2019 | Ramer | A61B 5/04001 |

OTHER PUBLICATIONS

Wikipedia, "Consumer Computer Brain-Interfaces", https ://en.wikipedia.org/wiki/Consumer _ brain%E2%80%93computer_ interfaces, searched Dec. 27, 2017 (2 pages).

Entire Prosecution History of U.S. Appl. No. 15/934,083, filed Mar. 23, 2018, entitled "Electroencephalography Control of Controllable Device".

Entire Prosecution History of U.S. Appl. No. 15/948,448, filed Apr. 9, 2018, entitled "Training of an Electroencephalography Based Control System".

Entire prosecution history of U.S. Appl. No. 16/217,543, entitled "Neural Control of Controllable Device," filed Dec. 12, 2018.

Sophia Chen, "Hardwiring the Brain fNIRS technology creates an increasingly sophisticated connection between brain and computer," SPIE Professional, Jan. 2019, pp. 22-24.

Osa®, "Fiber Optic Sensor Measures Tiny Magnetic Fields," Sep. 19, 2019, Copyright ©2018 The Optical Society (4 pages).

Non Final Office Action for U.S. Appl. No. 15/934,083, dated Aug. 9, 2019, 9 pages.

Notice of Allowance for U.S. Appl. No. 15/934,083, dated Oct. 9, 2019, 8 pages.

Non Final Office Action for U.S. Appl. No. 15/948,448, dated Oct. 22, 2019, 15 pages.

Notice of Allowance for U.S. Appl. No. 15/948,448, dated Feb. 13, 2020, 11 pages.

\* cited by examiner

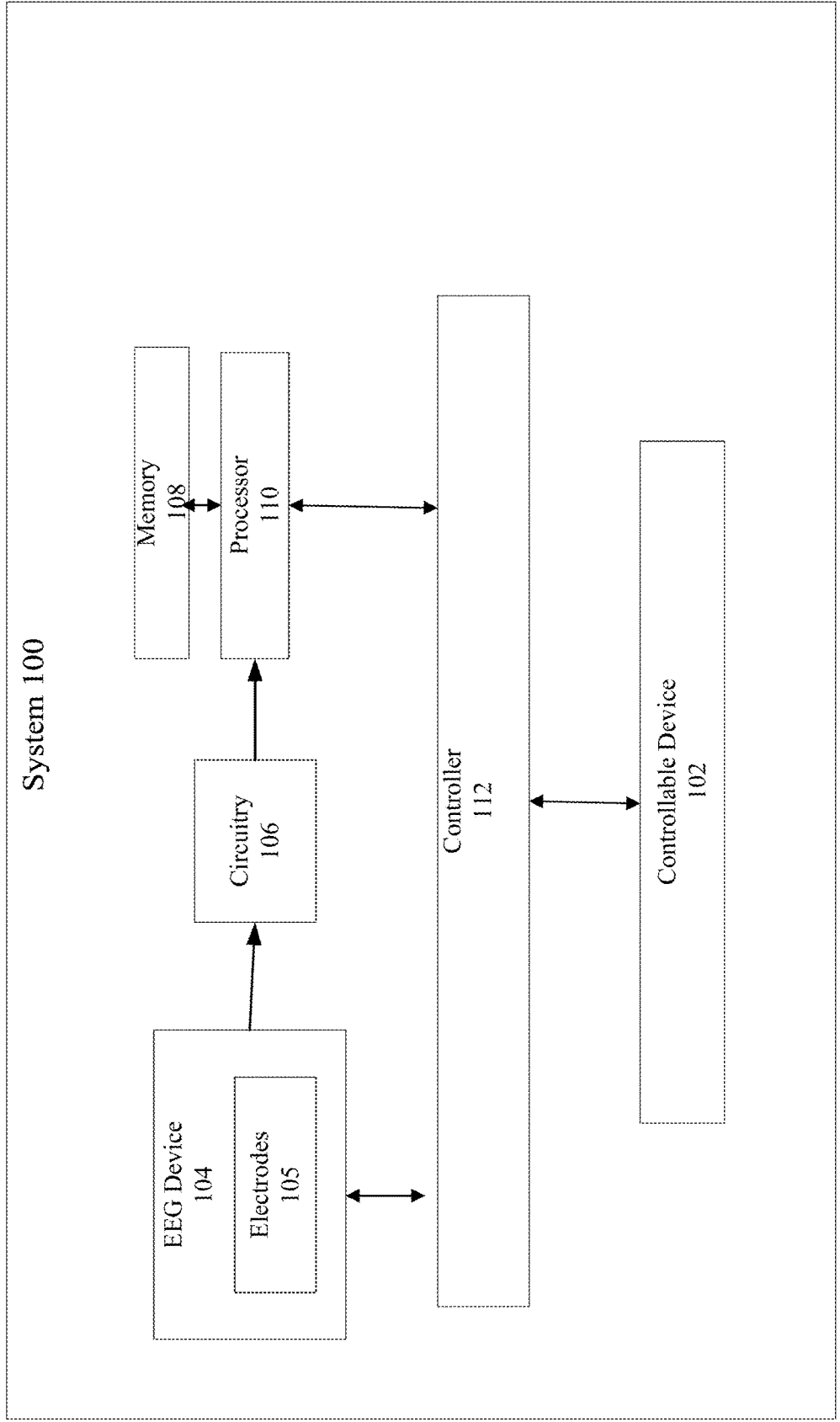

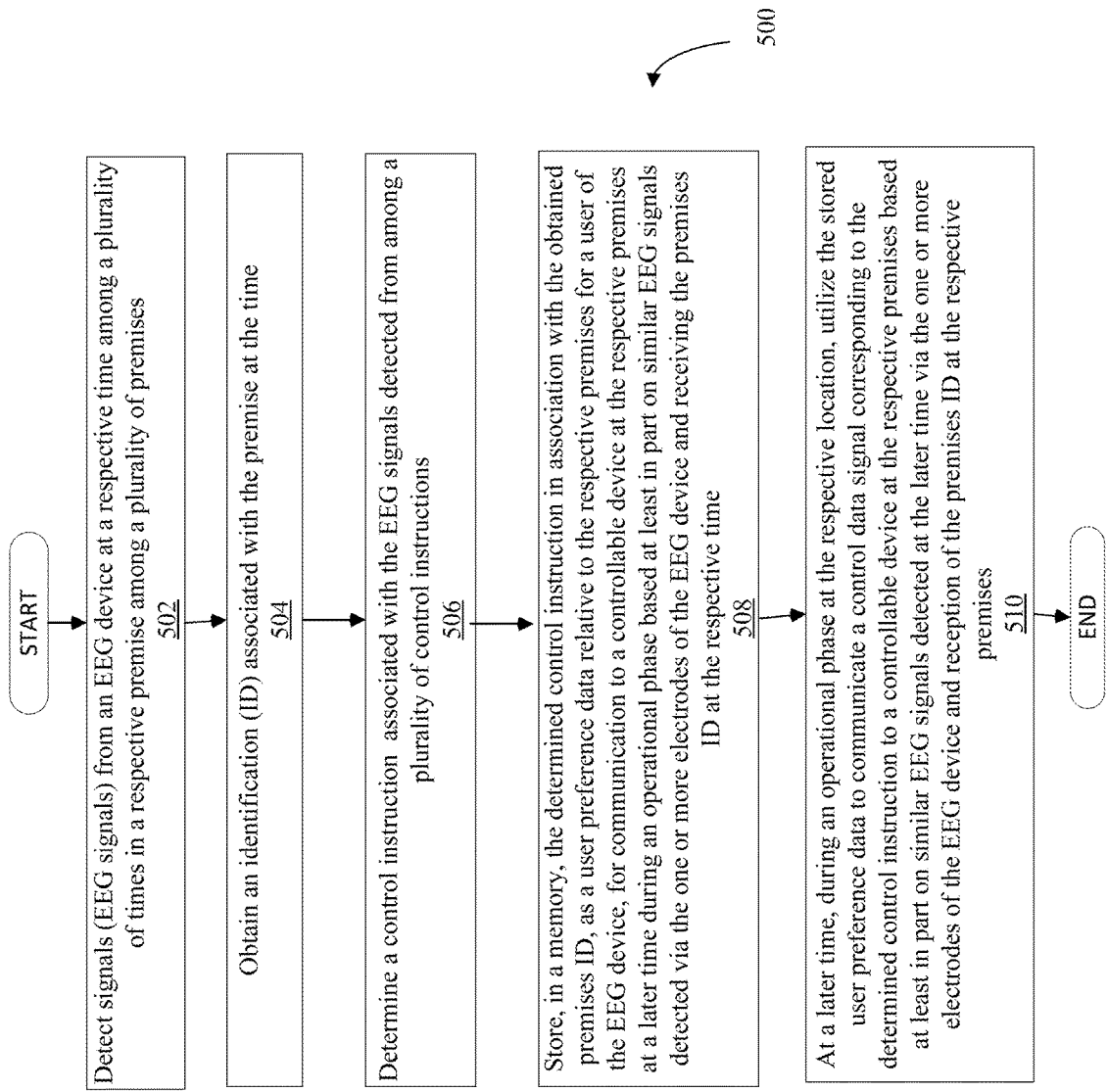

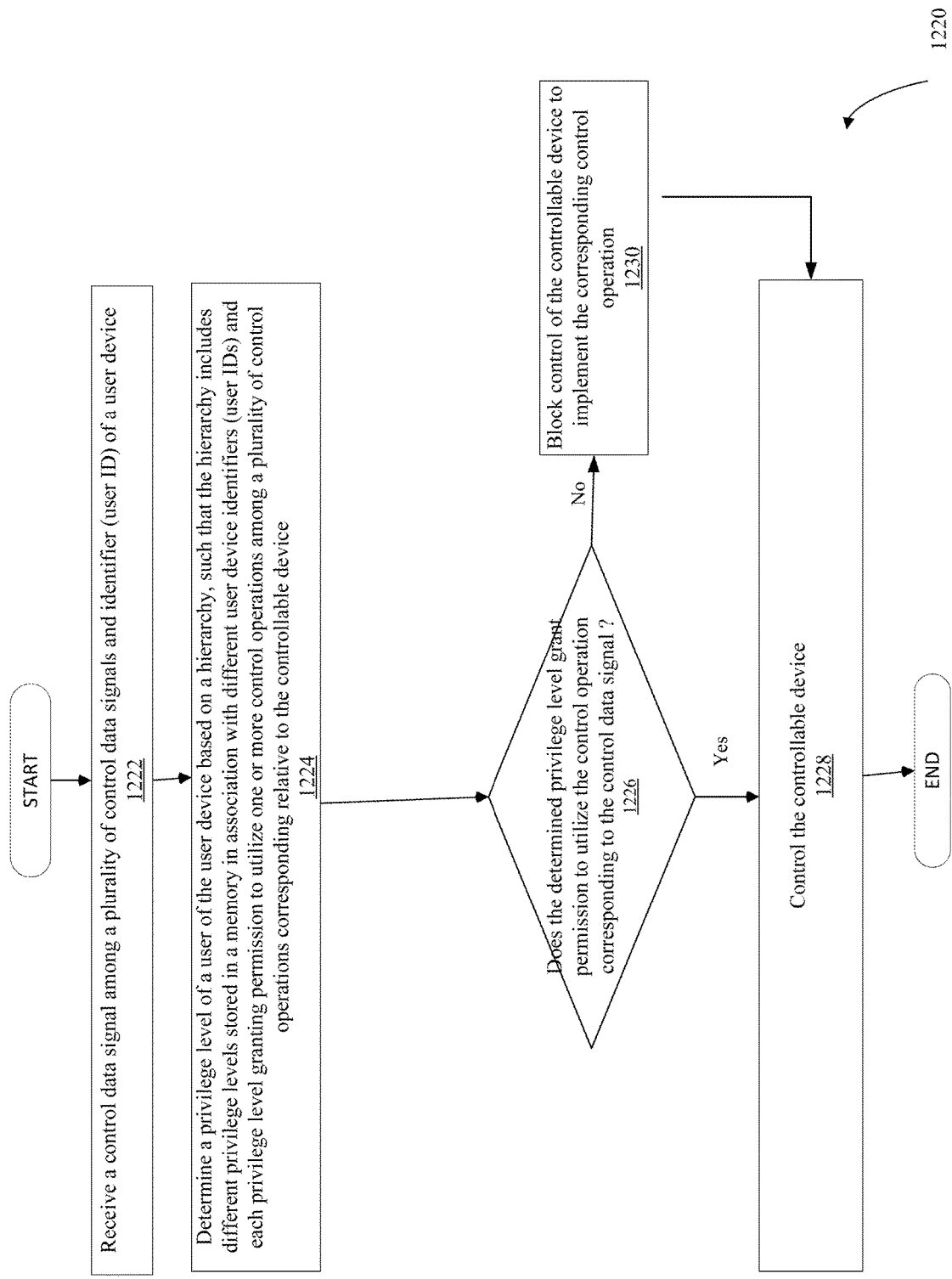

USER PREFERENCE AND USER HIERARCHY IN AN ELECTROENCEPHALOGRAPHY BASED CONTROL SYSTEM

CROSS-REFERENCE TO RELATED APPLICATIONS

This application is a Continuation-in-Part of U.S. patent application Ser. No. 15/934,083 filed Mar. 23, 2018, now allowed, entitled "ELECTROENCEPHALOGRAPHY CONTROL OF CONTROLLABLE DEVICE," and is also a Continuation-in-Part of U.S. patent application Ser. No. 15/948,448 filed Apr. 9, 2018, now pending, entitled "TRAINING OF AN ELECTROENCEPHALOGRAPHY BASED CONTROL SYSTEM," the entire contents of which both are incorporated herein by reference. Also, the Ser. No. 15/948,448 (pending) application is a Continuation-in-Part of the Ser. No. 15/934,083 (allowed) application.

TECHNICAL FIELD

The subject matter of this application is directed toward control systems, more specifically to user preference and user hierarchy in an Electroencephalography (EEG) system for control of lighting and/or building management systems (BMS).

BACKGROUND

Electroencephalography (EEG) is an electrophysiological monitoring method to record electrical activity of the brain. It is typically noninvasive, with the electrodes placed along the scalp, although invasive electrodes are sometimes used such as in electroencephalography (EEG) measures voltage fluctuations resulting from ionic current within the neurons of the brain. In clinical contexts, EEG refers to the recording of the brain's spontaneous electrical activity over a period of time, as recorded from multiple electrodes placed on the scalp. Diagnostic applications generally focus either on event-related potentials or on the spectral content of EEG. The former investigates potential fluctuations time locked to an event like stimulus onset or button press. The latter analyzes the type of neural oscillations that can be observed in EEG signals in the frequency domain.

It has been suggested to measure and record the brain's spontaneous electrical activity to configure the EEG for control of devices. For example, the U.S. Air Force demonstrated in the 1980s that pilots wearing simple EEG head gear could control computer displays. Such EEG is configured prior to controlling the computer displays during real-time operation. Presently, EEG systems are being configured to control things like "quad copters". In fact, EEG sensors may be implemented inside a head of a user. As this technology becomes more prevalent one could imagine that configuring of the EEG systems prior to real-time to control a wide range of equipment in the real-time operation could become pervasive.

In recent years, the sophistication of lighting control systems have increased significantly, for example, offering lighting scene, profile or schedule manipulation for individual lighting devices, for groups of lighting devices or all for lighting devices at a controlled premises. Depending on the technology of the luminaires, control functions may include simple ON/OFF control, intensity control (e.g. dimming) and even control of color characteristics (e.g. for tunable white luminaires or the like). Building Automation Control (BAC) systems or Building Management Systems (BMS) also have improved in the sophistication of the ability to reach every unit item or controllable appliance at the premises, offer informative, intuitive access to information and readily customizable control operations for every controllable device on the premises that is adapted for BAC or BMS type networked monitoring and control functions. Many such sophisticated lighting control and BAC systems are also configured with user's preferred settings for the control functions at the premises specific to the user. At least some of these systems may be configured with a user hierarchy granting different permissions to specific control functions based on a level of hierarchy assigned to each potential user.

Currently no such EEG systems exist that are configured with user preferences and user hierarchy based on the EEG for control of the lighting operations of the lighting systems and/or building management operations of the building management system. Further, no such EEG systems exist that provide for such user preferences or user hierarchy during real-time operation of the EEG device to control the light operations or the building management operations.

SUMMARY

The Examples disclosed herein improve over lighting control systems and BAC systems by providing EEG user preference related configuration methodology and/or user access hierarchy for real time operation control of lighting system and/or building management system functions.

An example system includes an electroencephalography (EEG) device configured to be positioned on a head of a user. The EEG device includes one or more electrodes configured to detect EEG signals from the brain of the user. The system also includes a circuitry coupled to the one or more electrodes configured to process the EEG signals detected via the one or more electrodes of the EEG device. The system also includes a processor coupled to or in communication with the circuitry. The system further includes a memory accessible by the processor and program instructions stored in the memory for execution by the processor such that the execution of the program instructions configures the processor to in an configuration phase, for each respective location among a plurality of locations at a respective time among a plurality of times, obtain an identification (ID) associated with the respective premises at the respective time; determine a control instruction associated with the EEG signals detected via the one or more electrodes of the EEG device, from among a plurality of control instructions; and store the determined control instruction in association with the obtained premises ID, as a user preference data relative to the respective location. At a later time, during an operational phase at the respective location, the processor is configured to utilize the stored user preference data to communicate a control data signal corresponding to the determined control instruction to a controllable device at the respective premises based at least in part on similar EEG signals detected at the later time via the one or more electrodes of the EEG device and reception of the premises ID at the respective premises.

Another example system includes a first processor coupled to or in communication with a controllable device to selectively provide a premises related service in a premises. The system also includes a receiver coupled to the first processor. The system also includes a first memory, accessible to the first processor and a hierarchy of different privilege levels stored in the first memory in association with different user device identifiers such that each privilege level granting permission to utilize one or more control operations among a plurality of control operations relative to the controllable device. The system also includes a user device including an electroencephalography (EEG) device configured to be positioned on a head of a user, such that the EEG device includes one or more electrodes configured to detect EEG signals from the brain of the user. The system also includes a circuitry coupled to the one or more electrodes configured to process the EEG signals detected via the one or more electrodes of the EEG device. The system also includes a transmitter compatible with the receiver and a second processor coupled to the transmitter and coupled to or in communication with the circuitry. The system further includes a second memory accessible by the processor storing an identifier of the user device and program instructions for the second processor such that execution the program instructions configures the second processor of the user device to generate a control data signal based on the detected EEG signals. The control data signal corresponds to a control operation among a plurality of control operations to control the controllable device. The second processor is also configured to transmit, via the transmitter, the control data signal and the identifier of the user device to the first processor. The first processor is configured to implement functions to receive the control data signal and the identifier of the user device via the receiver, determine a privilege level of the stored hierarchy applicable to the user based on the received identifier of the user device; and control the controllable device based on whether or not the determined privilege level grants permission to utilize the corresponding control operation.

A further example system includes a processor coupled to or in communication with a controllable device to selectively provide a premises related service a premises, a receiver coupled to the processor and a memory accessible to the processor. The memory stores a hierarchy of different privilege levels in association with different user device identifiers and each level having permission to one or more control operations among a plurality of control operations to control the controllable device. The system also includes a first user device including a first electroencephalography (EEG) device configured to be positioned on a head of a first user. The first EEG device includes one or more electrodes configured to detect EEG signals from the brain of a first user. The system further includes a first circuitry coupled to the one or more electrodes configured to process the EEG signals detected via the one or more electrodes of the first EEG device; a first transmitter compatible with the receiver; a first processor coupled to the first transmitter and coupled to or in communication with the first circuitry and a first memory accessible by the first processor storing an identifier of the first user device and program instructions. The program instructions configures the first processor of the first user device to generate a first control data signal based on the detected EEG signals. The first control data signal corresponds to a first control operation among a plurality of control operations to control the controllable device. The first processor is further configured to transmit, via the transmitter, the first control data signal and the identifier of the first user device to the processor. The system also includes a second user device including a second electroencephalography (EEG) device configured to be positioned on a head of a second user. The second EEG device includes one or more electrodes configured to detect EEG signals from the brain of a second user. The system further includes a second circuitry coupled to the one or more electrodes configured to process the EEG signals detected via the one or more electrodes of the second EEG device; a second transmitter compatible with the receiver; a second processor coupled to the second transmitter and coupled to or in communication with the second circuitry; and a second memory accessible by the second processor storing an identifier of the second user device and program instructions. The execution of the program instructions configures the second processor of the second user device to generate a second control data signal based on the detected EEG signals. The second control data signal corresponds to a second control operation among the plurality of control operations to control the controllable device. The second control operation is different from the control operation. The second processor is further configured to transmit, via the second transmitter, the second control data signal and the identifier of the second user device to the processor. The processor is configured to access the memory to execute program instructions stored in the memory such that execution of the program instructions configures the processor to receive the first control data signal including the identifier of the first user device and the second control data signal including the identifier of the second user device via the receiver; determine a privilege level of the stored hierarchy applicable to the first user based on the received identifier of the first user device and a privilege level of the stored hierarchy applicable to the second user based on the received identifier of the second user device; compare the privilege level of the second user with the privilege level of the first user; and implement a selected one of the first control operation or the second control operation relative to the control of the controllable device based on a result of the comparison.

An example method includes detecting EEG signals from an EEG device at a respective time among a plurality of times during a configuration phase and in a respective premises among a plurality of premises; obtaining an identification (ID) associated with the premises at the respective time; determining a control instruction associated with the EEG signals detected from among a plurality of control instructions; storing, in a memory, the determined control instruction in association with the obtained premises ID, as a user preference data relative to the respective premises for a user of the EEG device, for communication to a controllable device at the respective location at a later time during an operational phase based at least in part on similar EEG signals detected via the one or more electrodes of the EEG device and receiving the premises ID at the later time; and at a later time, during the operational phase at the respective location, utilizing the stored user preference data to communicate a control data signal corresponding to the determined control instruction to a controllable device at the respective premises based at least in part on similar EEG signals detected at the later time via the one or more electrodes of the EEG device and reception of the premises ID at the respective premises.

Another example method includes receiving a control data signal among the plurality of control data signals and identifier (user ID) of a user device; determining a privilege level of a user of the user device based on a hierarchy. The hierarchy includes different privilege levels stored in a memory in association with different user device identifiers (user IDs) and each privilege level granting permission to utilize one or more control operations among a plurality of control operations corresponding relative to the controllable device. The method also includes determining whether the privilege level controlling the device based on the determined privilege level grants permission to utilize the control operation corresponding to the control data signal; and controlling the controllable device based on whether or not the determined privilege level grants permission to utilize the corresponding control operation.

A further example method includes receiving a first control data signal including an identifier (user ID) of a first user device identifying a first user and a second control data signal including the user ID of a second user device identifying a second user; determining a privilege level of a stored hierarchy applicable to the first user based on the received user ID of the first user device and a privilege level of the stored hierarchy applicable to the second user based on the received user ID of the second user device such that the stored hierarchy includes hierarchy of different privilege levels stored in a memory in association with different user IDs and each privilege level granting permission to utilize one or more control operations among a plurality of control operations relative to control a controllable device; comparing the privilege level of the second user with the privilege level of the first user; and implementing a selected one of a first control operation among the plurality of control operations corresponding to the first control data signal or a second control operation among the plurality of control operations corresponding to the second control data signal relative to the control of the controllable device based on a result of the comparison.

Additional objects, advantages and novel features of the examples will be set forth in part in the description which follows, and in part will become apparent to those skilled in the art upon examination of the following and the accompanying drawings or may be learned by production or operation of the examples. The objects and advantages of the present subject matter may be realized and attained by means of the methodologies, instrumentalities and combinations particularly pointed out in the appended claims.

BRIEF DESCRIPTION OF THE DRAWINGS

The drawing figures depict one or more implementations in accord with the present teachings, by way of example only, not by way of limitation. In the figures, like reference numerals refer to the same or similar elements.

FIG. 1A illustrates another example of an EEG system, which may be configured with user preferences and utilize the user preferences in a real-time operational phase in an EEG based control of a premises related service in a premises.

FIG. 5 is an example flowchart illustrating a method for system level configuration of an EEG based system for controlling a premises related service provided by a controllable device in an area of a premises.

FIG. 12A is an example flowchart illustrating a method for providing user hierarchy and utilizing the user hierarchy in an EEG based system for controlling a premises related service provided by a controllable device in an area of a premises.

DETAILED DESCRIPTION

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings.

The term "luminaire" as used herein is intended to encompass essentially any type of device that processes generates or supplies light, for example, for general illumination of a space intended for use of or occupancy or observation, by a person or animal. However, a luminaire may provide light for use by automated equipment, such as sensors/monitors, robots, etc. that may occupy or observe the illuminated space, instead of or in addition to light provided for an organism. However, it is also possible that one or more luminaires in or on a particular premises have other lighting purposes, such as signage for an entrance or to indicate an exit. In most examples, the luminaire(s) illuminate a space or area of a premises to a level useful for a human in or passing through the space, e.g. general illumination of a room or corridor in a building or of an outdoor space such as a street, sidewalk, parking lot or performance venue.

The term "coupled" as used herein refers to any logical, physical or electrical connection, link or the like by which signals, data, instructions or the like produced by one system element are imparted to another "coupled" element. Unless described otherwise, coupled elements or devices are not necessarily directly connected to one another and may be separated by intermediate components, elements or communication media that may modify, manipulate or carry the signals. For example, system elements may be coupled for wired or wireless communication, including without limitation radio frequency (RF), light fidelity (LiFI), fiberoptic, ultrasonic or the like in the discussions below.

Various examples disclosed herein relate to an EEG methodology for a system configured to control lighting and building management. Examples described below encompass systems utilizing EEG configuration of the user preferences and real-time operational functionality utilizing the user preferences and/or the user hierarchy to control various BAC appliances, lighting devices, etc. that control a service in an area of a premises. Such service may include but is not limited to light, heating, ventilation and air conditioning (HVAC), door access, fire and safety equipment, on-premises surveillance, etc.

Reference is now made in detail to the examples illustrated in the accompanying drawings and discussed below.

Figure 1:
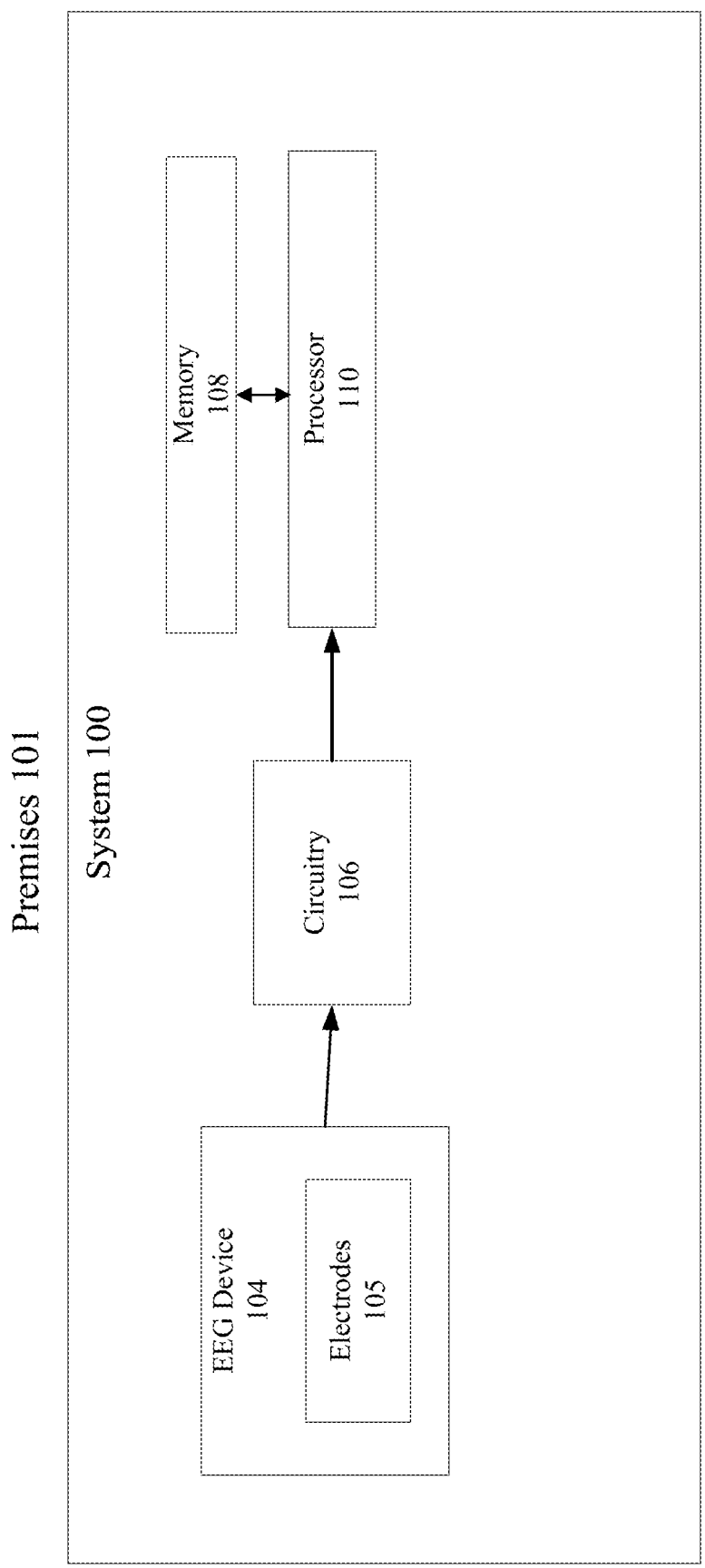
FIG. 1 illustrates one example of an EEG system for control of a premises related service in a premises.

The example of FIG. 1 illustrates an example of EEG system (system) 100 for control of a premises related service in a premises or location 101. Some of the premises related services include but are not limited to light, heating, ventilation and air conditioning (HVAC), door access, fire and safety equipment, on-premises surveillance, etc. In one example, the premises 101 is identified by a location identification (ID) that is unique to the location. Although, a single premises 101 is shown, it is known to one of ordinary skill, that the EEG system 100 is configured with user preferences in multiple locations such that each location in the multiple locations is assigned with its unique ID to differentiate with other multiple locations (See FIG. 6C). In one example, the memory 108 stores the location ID associated with each of the multiple premises.

The system 100 includes an electroencephalography (EEG) device 104, which is configured to be positioned with respect to a head of a user in the premises 101. In one example, the EEG device 104 is an EEG headset placed on top of the user's head. In another example, the EEG device 104 is an EEG sensor implanted inside the user's head. The EEG device 104 includes one or more electrodes 105 configured to detect signals from a brain of the user. The system 100 also includes a circuitry 106 coupled to the electrodes 105 to process the signals detected by the electrodes 105. In one example, the signals are sets of signals detected by the electrodes 105 in real time. In one example, the signals are EEG signals detected by the electrodes 105 prior to real time. In another example, the signals are sets of neural signals (e.g. nerve signals (see FIGS. 9 and 10) alone or in combination with EEG signals. In one example, the EEG device 104 is assigned with a user identification data that identifies the user of the device. Although, a single EEG device 104 is shown, it is known to one of ordinary skill, that the EEG system 100 is configured with user preferences associated with multiple EEG devices (See FIG. 6D) such that each EEG device among the multiple EEG devices is assigned with its unique user identification (ID) to differentiate with other multiple EEG devices to identify the user of the EEG device among multiple users of the EEG device. In one example, the memory 108 stores the user ID associated with each of the multiple EEG devices.

In one implementation, the system 100 includes a memory 108 that stores data, which includes a plurality of control instructions. A control instruction corresponds to controlling the premises related service provided in the premises 101. The system 100 also includes a processor 110, which is coupled to the circuitry 106 to receive the processed sets of detected EEG signals. The memory 108 also stores program instructions, which is accessible by the processor 110. In one implementation, the processor accesses the program instructions to perform various functions at a plurality of times in a configuration phase, as described herein.

In one implementation, at the premises 101, during the configuration phase, the processor 110 at a respective time t among the plurality of times analyzes the detected EEG signals to determine that the detected EEG signals correspond to a control instruction among the plurality of control instructions stored in the memory 108. In one example, the currently detected EEG signals are compared to pre-determined sets of signals that correspond to the various available control instructions, and the processor recognizes correspondence of detected signals to an instruction if the currently detected EEG signals match a predetermined set of signals associated with a particular instruction, to within some appropriate tolerance. Upon detecting such correspondence, data is stored in the memory to associate the control instruction (and/or the pre-determined set of signals that corresponded to the detected EEG signals with the location ID at the respective time t. The processor 110 further stores for the user ID in the memory 108, data as user preference data including the control instruction corresponding with the location ID and the respective time t.

In one example, in a training mode, the system updates the data such as the pre-determined set of signals and corresponding control instruction when the real-time EEG signals are not recognized as known control instruction. For example, the system updates the pre-determined set of signals based on an input from a trusted detector indicating the type of control instruction user intended in the real-time detected EEG signals. Further, in the training mode, the configuration and/or settings are provided to help the EEG device and/or a PIOT device to learn to associate the signals with user's desired control instruction In another implementation, the memory 108 also stores instructions, which are accessible by the processor 110 such that in an operational phase, execution of the instructions by the processor 110 to perform various functions described herein.

In one implementation, during the operational phase, the processor 110 detects the EEG signals from the EEG device 104 in the premises 101 at a later respective time t and accesses the memory 108 to retrieve the user preference data associated with the EEG device 104. As discussed above, the user preference data includes the control instruction associated with the premises 101. In one example, the processor 110 determines that currently detected EEG signals for the user ID correspond to the control instruction (sufficiently match the corresponding pre-defined set of signals). The processor 110 also detects reception of the associated location ID of the premises 101. The processor 110 generates a control data signal associated with the control instruction. The control data signal corresponds to a control operation among a plurality of control operations of a controllable device (see FIG. 1A) configured to perform the control operation. The control operation controls the premises related service in the premises 101, in this case, in accordance with the user's preference.

In one example, the user thinks 'brighter' and the processor 110 detects the EEG signals based on the user's thought to determine the corresponding control instruction. the processor 110 generates the control data signal corresponding to the control data signal and sends the control signal so that the controller/controllable device turns up the light intensity (because the preference is to increase light, and the configuration includes knowledge of the premises system specific instruction/control data signal for that function and effectively that the system at the particular premises has dimmable lights). At another premises without dimmable lights, the user may have the same thought, which might normally equate to a turn-ON command (the only/preferred option), in which case no signal is sent or the system ignores the control data signal if the light are already ON.

In one implementation, the processor 110 determines that the detected EEG signals for the user ID do not correspond to the control instruction associated with the premises ID of the premises 101 at the later respective time t. The processor 110 analyzes the detected EEG signals to determine that the detected EEG signals correspond to another control instruction among the plurality of control instructions stored in the memory 108. The processor 110 updates the user preference data for the user ID in the memory 110 to associate other control instruction with the premises ID of the premises 101. In one implementation, the processor 110 replaces the control instruction with other control instruction in the user preference data stored for the user ID in the memory 108. The processor 110 generates another control data signal associated with other control instruction. Other control data signal corresponds to another control operation among the plurality of control operations of a controllable device (see FIG. 1A) configured to perform other control operation, which is different from the control operation. These types of operations may be thought of as implementing a later configuration or learning phase to update the associations to EEG signals for different preferences over time.

In one implementation, during the operational phase, the EEG device 104 continuously/repeatedly detects the EEG signals in the premises 101 during each respective cycle of time t. In one implementation, the processor 110 repeatedly analyzes the EEG signals to determine that the EEG signals either correspond to the associated control instruction in the user preference data or do not correspond to the associated control instruction in the user preference data for the identified premises 101 at the respective time t. In one example, the processor 110 analyzes the EEG signals ten times in the premises 101 during the respective time t. In one scenario, the processor 110 determines that the EEG signals correspond to the associated control instruction in the user preference data at least seven out of ten times. In that case, the processor 110 generates the control data signal based on the associated control instruction, as outlined above. In another scenario, the processor 110 determines that the EEG signals do not correspond to the associated control instruction in the user preference data at least seven out of ten times. In that later case, the processor 110 determines that the EEG signals correspond to other control instruction and thus updates the control instruction in the user preference data with other control instruction to associate with the location ID as part of the configuration update phase in time t.

FIG. 1A includes another example of the EEG system 103, which includes the same components of system 100 and further includes a controllable device 102 and a controller 112. As illustrated, the controller 112 is coupled to or in communication with the controllable device 102 and the processor 110. Such controllable device 102 may include luminaire, various BAC appliances etc. In one example, the controllable device 102 is a luminaire such that the control instruction provides instruction on controlling the luminaire. In another example, the controllable device 102 is a BAC appliance such that the control instruction provides instruction on controlling the BAC appliance. The processor 110 selects one of the luminaire or the BAC appliance based on the control instruction. The processor 110 generates a control data signal for the selected luminaire or the BAC appliance based on the at least one control instruction. In one example, the controller 112 is an intelligent element integrated in the controllable device 102. In another example, that the controller is a centralized controller controlling a plurality of similar controllable devices, (e.g. wall switch or like controlling a number of the luminaires or a building management control system (control the controllable device and other types of devices within the premises).

In one implementation, during the operational phase, the processor 110 transmits the control data signal to a controller 112, which controls the premises related service provided by the controllable device 102 (selected luminaire or the BAC appliance) in the area 101. In one implementation, the controller 112 controls the premises related service in a real time operational phase. Some examples of controlling the premises related services include but are not limited to turning lights on or off, dimming lights, color temperature, color red green blue, circadian rhythm, chaotic program, individual luminaire control, occupancy sensing, decrease or increase level of one of heating, cooling or air, open or close doors, open or close the doors, turn on or off the television, decrease or increase the sound of alarm system etc.

In one implementation, the EEG device 104 is configured or provisioned to generate and send the control instruction in an appropriate format for controlling the lighting system or the BAC appliance system in the area 101. In one implementation, the EEG configuration is repeated when the EEG device 104 is located in a premises or location that is different from the premises 101 utilizing another system that is different from the system 100 (See FIG. 6C). In one implementation, at a different area, the EEG device 104 is configured or provisioned to operate with the different system at the different area or location. Provisioning of a device to operate on a network usually entails some input of data to the device and/or the network to set up device communications via the network. If the device supports multiple communication bands and protocols, the provisioning may also inform the device which band(s) and/or what protocol to use for control communications at the premises. If also needed, configuration may involve storing profile data or the like in the device and/or the network defining user privileges when using the system and/or providing access to some or all of the control services the system offers that will available to the user of the particular device. For example, a user of the EEG device 104 is provided with configuration or provisioning data for the different system with options to select to configure the EEG device 104 with the different system in the different premises. As such, the EEG device 104 may be used at multiple different premises with multiple different lighting systems and/or BAC appliance systems, based upon provisioning or commissioning for operation on each system.

In one implementation, a controller or controllable devices stores a plurality of different hierarchical classes or levels of user(s) as member(s) with each level having permissions to use one or more control instructions among the plurality of control instructions. Some examples of levels of users include, building administrator, employee, guest etc. For example, the building administrator has permissions to use all the control instructions while the guest may only have permissions to one or two control instructions, such as to turn ON the lights in a dark room (e.g. to provide the guest with light in the event that the occupancy sensor in the room fails to do turn the lights ON).

In another implementation, hierarchical class or level of the user(s) is established and/or changed based on other factors such as location/premises, situations or circumstances taking place at the premises, policies and/or procedures of the premises, activity at the premises, day, time etc. that take priority over the user's hierarchical class or level. For example, a user A has a higher hierarchy level than the user B in user A's office and user A is outside his/her office and sends a control instruction to turn off the lights while the user B is still in the user A's office. In such scenario, the hierarchy level will be changed such that the user B will be assigned priority over the user A as having the permissions to use one or more control instructions (e.g. turn on the lights or keep the lights on) in the user A's office. As such, hierarchical class or level of the user(s) is replaced with priority based on such factors. In another implementation the controller or controllable devices stores a plurality of different priority levels based on such factors.

In one implementation, the data communication receiver 209 receives a user identification data from the EEG device 104, for example, an identifier of the EEG device itself or of the PIOT device. In one implementation, the data communication receiver 209 receives a user identification data directly from the PIOT device 220. The processor 110 utilizes the received user identification data to search the memory 108 to identify the user among the plurality of users and the corresponding hierarchy level of the identified user of which the user is the member. In one implementation, the processor 110 transmits the control data signal to the controller 112 that relates to the one or more control instructions if permitted for the corresponding hierarchy level. The controller 112 controls the premises related service provided by the controllable device 102 (selected luminaire or the BAC appliance) in the area 101 based on the permitted one or more control instructions.

Figure 1B:
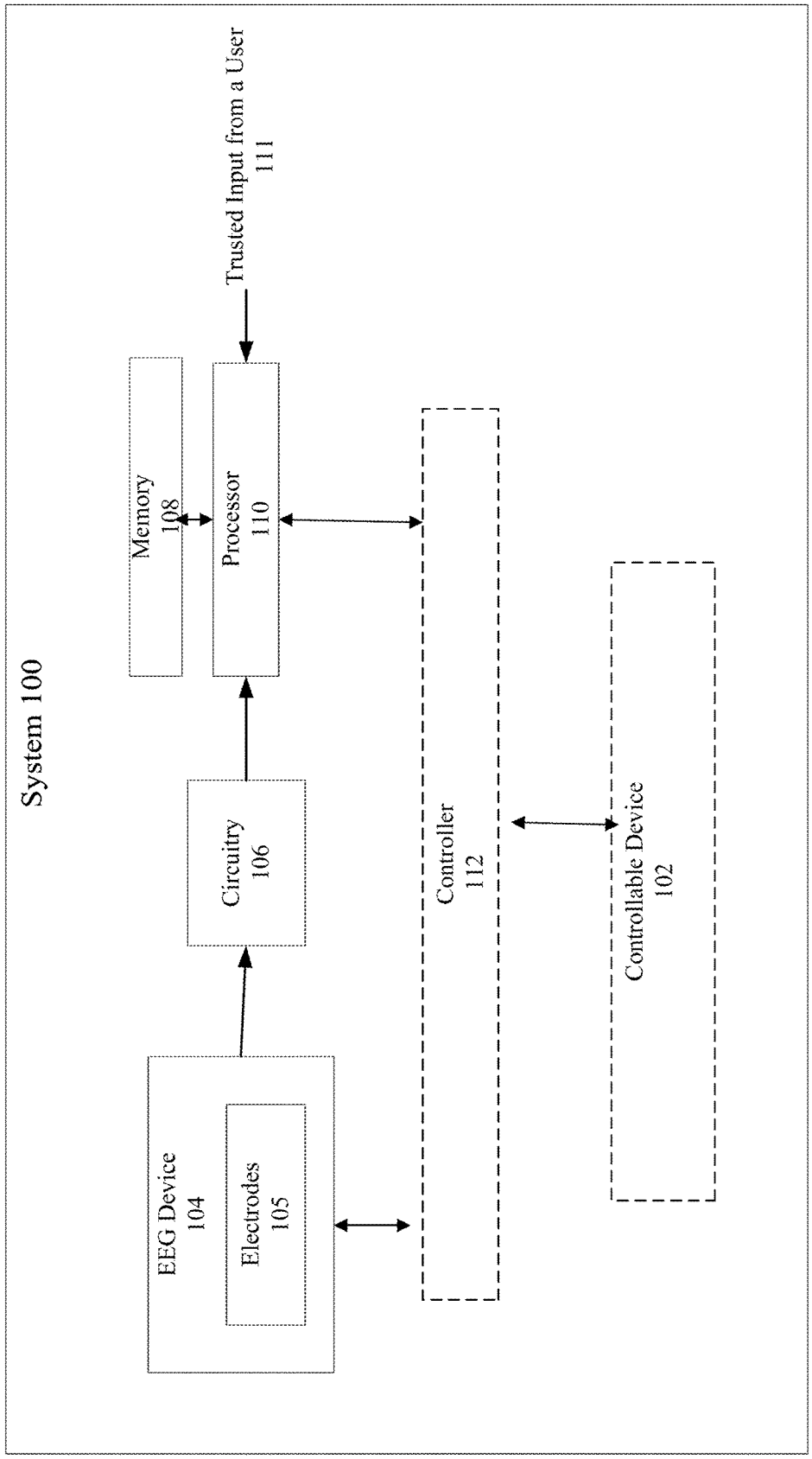
FIG. 1B illustrates a further example of an EEG system, which may be configured with user preferences and utilize the user preferences in a real-time operational phase in an EEG based control of a premises related service in a premises.

FIG. 1B includes another example of the system 105, which includes the same components of system 100 and further includes a trusted input 111 from a user (e.g. via user interface device). In one example, the user is the user of the EEG device 104. As discussed above, the user preference data includes the control instruction associated with the premises 101 and the respective time t. In one implementation, during the operational phase, the processor 110 sends the user preference data to the user of the EEG device via a user device e.g. a display device, an audio device or a haptic device (See FIG. 2). The processor 110 receives the trusted input 111 from the user of the EEG device 104 at the premises 101 at the later respective time t.

In one example, the trusted input is a positive trusted input, which includes a user's approval of the control instruction in the user preference data. In another example, the positive trusted input may include user selection of the control instruction in the user preference data. In one implementation, during the operational phase, the processor 110 receives the positive trusted input as the trusted input. As a result, the processor 110 generates the control data signal corresponding to the control instruction in the premises 101 in real-time operational phase. In one example, the trusted input includes a negative trusted input, which includes a user's disapproval of the control instruction in the user preference data. In another example, the negative trusted input includes a user's selection of another control instruction among the plurality of control instructions. This another control instruction is different from the control instruction corresponding to the control data signal generated by the processor 110. As a result, the processor 110 modifies the user preference data by replacing the control instruction with other control instruction in association with the premises 101 in real-time operational phase. The processor 110 further generates another control data signal corresponding to other control instruction in the premises 101 in real-time operational phase. Other control data signal corresponds to another control operation among the plurality of operations. This another control operation is different from the control operation.

In one implementation, the trusted input is received via a user responsive element. In one example, the user responsive element is a user device with input capability and output capability (e.g. a display device, an audio device or a haptic device (See FIG. 2). Examples of such user devices may include mobile devices, desktop or portable personal computers or similar computer devices, or user devices specifically configured for use preferences in the EEG based system. In another example, the user responsive element is a manual control of a controllable device (See FIG. 1A) by the user. For example, the control operation functionality associated with control instruction in the user preference data may result in the control data signal, which is transmitted to a controller (See FIG. 1A), which functions to automatically turn off the lights in the premises 101, and the user of the EEG device 104 manually operates a wall switch or button or the like to turn on the lights. The processor 110 might interpret the manual operation to turn on the lights right after system turn off of the lights, i.e. another control operation, as a disapproval or other negative trusted input. The system might then undo the previous operation and/or update user preference data with other control instruction corresponding other control operation as part of the configuration during the operational phase. In one example, the control data signal associated with another control operation of turning on the lights is sent and received via a RF transceiver of a network (not shown).

In one example, the user responsive element is a function of the EEG device 104 such that the trusted input (positive or negative) is based on detection of EEG signals indicating one or more of the approval of the control instruction, disapproval of the control instruction, selection of the control instruction and selection of another control instruction, which is different from the control instruction, as discussed above. In another example, the user responsive element is a reaction or behavior of the user of the EEG device 104 such that the trusted input (positive or negative) is received as a function of the reaction or behavior of the user of the EEG device 104. For example, the user of the EEG device 104 may indicate satisfaction (e.g. smile by the user or nod by the user), which is interpreted as positive trusted input, i.e. the approval of the control operation corresponding to the control instruction in the user preference data. In another example, the user of the EEG device 104 may indicate annoyance (e.g. roll his eyes or shake his head), which is interpreted as the negative trusted input, i.e. disapproval of the control operation corresponding to the control instruction in the user preference data. In a further example, the user responsive element is a gesture (e.g. some type of movement) by the user of the EEG device 10 such that the trusted input (positive or negative) is received as a function of the gesture by the user of the EEG device 104. For example, the control operation functionality results in control data signals which is transmitted to a controller (see FIG. 1A), which functions to automatically turns off the lights and the user raises her hand, which is interpreted as turn on the lights, i.e. another control operation.

In one implementation, a passive acceptance by a user is interpreted as the positive trusted input, i.e. the approval of the control operation corresponding to the control instruction in the user preference data. For example, the user of the EEG device 104 is inactive (i.e. does not take any action related to the control operation corresponding to the control instruction in the user preference data or use the responsive element to indicate any type of the trusted input) in response to the control operation corresponding to the control instruction in the user preference data, which is interpreted as the positive trusted input.

In one implementation, during the operational phase, the processor 110 continues to receive the trusted input at the location 101. In one implementation, the processor 110 continuously/repeatedly determines that the trusted input is either one of the positive input corresponding to approval of the associated control instruction in the user preference data or a negative input corresponding to disapproval of the associated control instruction in the user preference data in the premises 101. In one example, the processor 110 receives the user input ten times. In one scenario, the processor 110 receives a positive trusted input at least seven out of ten times. The processor 110 generates the control data signal based on the associated control instruction. In another scenario the processor 110 receives a negative trusted input at least seven out of ten times. The processor 110 modifies the user preference data by replacing the control instruction with other control instruction selected by the user. The processor 110 generates another control data signal, different from the control data signal, based on other control instruction. Alternatively, the system 105 may also include the controllable device 102 and the controller 112 of the system 103 of FIG. 1A. As discussed above, the controller 112 is coupled to or in communication with the controllable device 102 and the processor 110. Such controllable device 102 may include luminaire, various BAC appliances etc. Also discussed above, in one implementation, during the operational phase, the processor 110 transmits the control data signal to a controller 112, which controls the premises related service provided by the controllable device 102 (selected luminaire or the BAC appliance) in the premises 101. Also, as discussed above, in one implementation, the controller 112 controls the premises related service in a real time operational phase. Further, in one implementation, the EEG device 104 is configured or provisioned to generate and send the control instruction in an appropriate format for controlling the lighting system or the BAC appliance system in the premises 101 as discussed in detail above.

Figure 2:
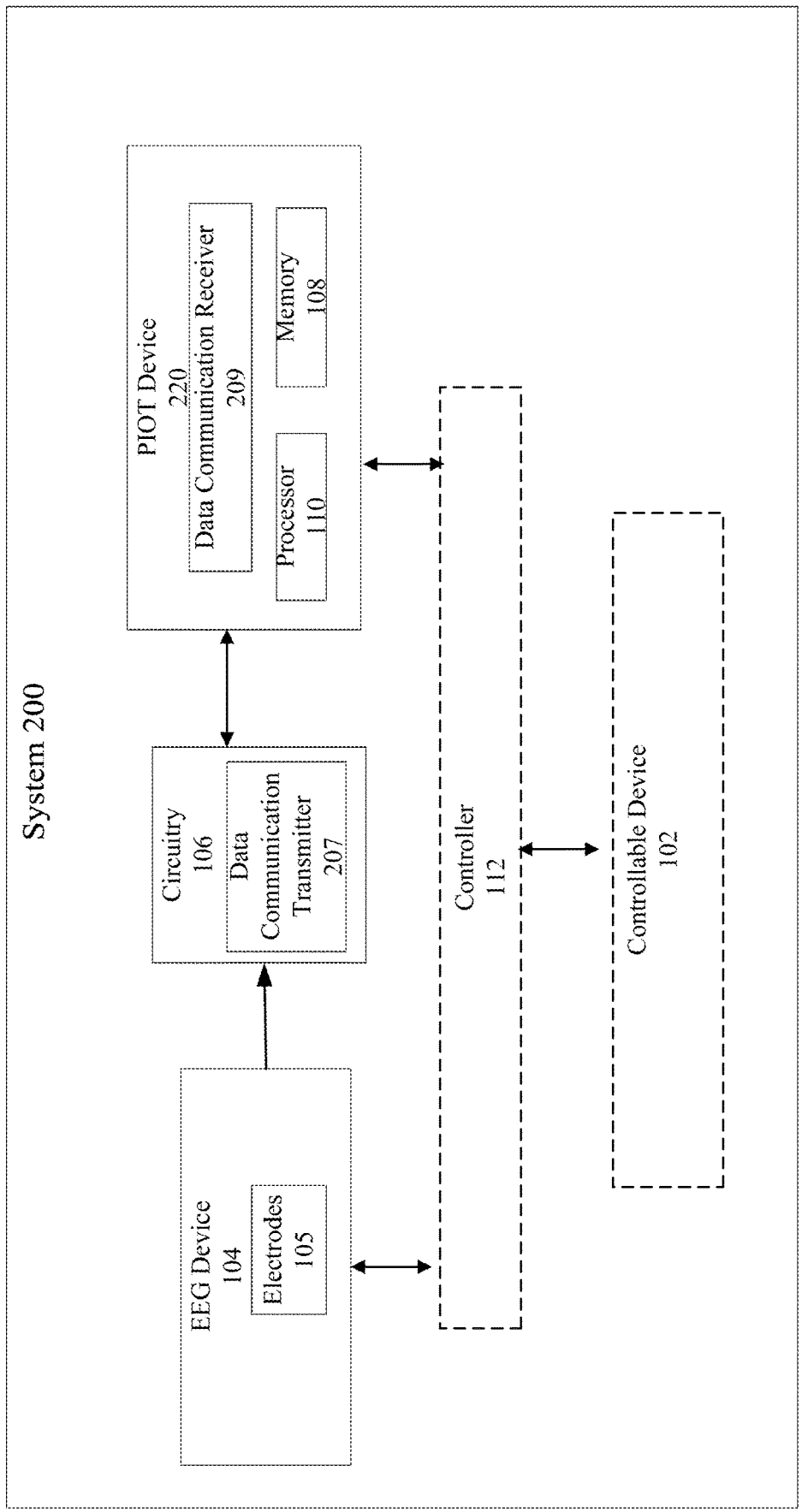
FIG. 2 illustrates another example of an EEG system for control of a premises related service in a premises.

FIG. 2 illustrates another example of an EEG system (system) 200 for control of premises related service in the premises 101. As shown, the system 200 includes the same components of system 100 and the circuitry 106 further includes a data communication transmitter 207. The system 200 also includes a personal Internet of Things (PIOT device) 220 including the memory 108 and the processor 110 and further including a data communication receiver 209. The data communication receiver 209 is compatible with the data communication transmitter 207 of the circuitry 106. In one example, the data communication transmitter 207 is a radio frequency (RF) transmitter configured to transmit data over RF spectrum. In another example, the data communication receiver 209 is a RF receiver configured to transmit data over the RF spectrum.

The RF spectrum or "radio spectrum" is a non-visible part of the electromagnetic spectrum, for example, from around 3 MHz up to approximately 3 THz, which may be used for a variety of communication applications, radar applications, or the like. In the discussions above, the RF transmitted and received for network communication, e.g. Wifi, BLE, Zigbee etc., was also used for controlling lighting or a building management control system, in the frequencies bands/bandwidths specified for those standard wireless RF spectrum data communication technologies. In another implementation, the network communications media may be wired, fiberoptic, LiFI, ultrasonic or the like.

In another implementation, the transceiver is an ultra-wide band (also known as UWB, ultra-wide band and ultraband) transceiver. UWB is a radio technology that can use a very low energy level for short-range, high-bandwidth communications over a large portion of the radio spectrum. UWB does not interfere with conventional narrowband and carrier wave transmission in the same frequency band. Ultra-wideband is a technology for transmitting information spread over a large bandwidth (>500 MHz) and under certain circumstances be able to share spectrum with other users. Ultra-wideband characteristics are well-suited to short-distance applications, such as short-range indoor applications. High-data-rate UWB may enable wireless monitors, the efficient transfer of data from digital camcorders, wireless printing of digital pictures from a camera without the need for a personal computer and file transfers between cell-phone handsets and handheld devices such as portable media players. UWB may be used in a radar configuration (emitter and deflection detection at one node) for real-time location systems and occupancy sensing/counting systems; its precision capabilities and low power make it well-suited for radio-frequency-sensitive environments. Another feature of UWB is its short broadcast time. Ultra-wideband is also used in "see-through-the-wall" precision radar-imaging technology, precision detecting and counting occupants (between two radios), precision locating and tracking (using distance measurements between radios), and precision time-of-arrival-based localization approaches. It is efficient, with a spatial capacity of approximately 1013 bit/s/m$^2$. In one example, the UWB is used as the active sensor component in an automatic target recognition application, designed to detect humans or objects in any environment.

In one example, the user ID is uniquely associated with the EEG device 104 identifying a user among a plurality of users of the EEG device 104 in the area 101 of the premises. In another example, the user ID is uniquely associated with the PIOT device 220 identifying a user of the PIOT device 220 identifying a user among the plurality of users of the PIOT device 220 in the area 101 of the premises. The user's location is tracked based on the user ID associated with one or both of the EEG device 104 or the PIOT device 220. In one implementation, having a unique ID for each EEG device 104 and PIOT device 220 may not necessarily protect the lighting/BMS controls from exploits carried out by someone who has unauthorized access to these devices. As an example, user A who is the lowest in the hierarchy and priority scheme can still carry out privileged control actions if he/she gets access to the EEG device 104 and/or the PIOT device 220 (EEG-PIOT device) that belongs to user B who ranks the highest in the hierarchy and priority scheme. If the EEG-PIOT device can generate a signature of the person from his/her EEG signals or some other biometric data gathered by the PIOT device he/she is wearing, that can be used to authenticate the user and allow/disallow control through the EEG-PIOT device for that particular user. This way, only the owner of the EEG-PIOT device can operate it. In one example, the EEG-PIOT device communicates with an associated cloud service or a local service to get user permissions anytime a different user's EEG-PIOT biometric signature is detected. Thus, anyone can get his/her controls independent of the EEG-PIOT device he/she is using. This way, user A still has the same control permissions as with his EEG-PIOT device despite using user B's EEG-PIOT device that he/she acquired without authorization. Accordingly, one can easily adapt to changes in hierarchy and priority since permissions and policies may be managed at a remote server, which also allows the users to temporarily grant control permissions to other users more easily as well as the facility administrators to revoke permissions for certain users with ease.

In one implementation, the data communication receiver 209 receives identifying data from the controller 112. The identifying data includes but is not limited to location of the controller in the area, communication capabilities of the controller, control operations supported by the controller, types of controllable devices controlled by the controller, controller variables for each type of controllable device, or combinations thereof.

In one example, the communication capabilities are supported by the EEG device 104. In another example, the communication capabilities are supported by the PIOT device 220. The control operations supported by the controller may include light related control operations, building related control operations etc. Some of the light related control operations include turning lights on/off, dimming lights, color temperature, color red green blue, circadian rhythm, chaotic program etc. Building related control operations include heating/cooling & air control, door access controls, fire and safety control, on-premises surveillance control etc. As discussed above, type of controllable device includes luminaire, various BAC appliances etc. The controllable variables for each type of the controllable device are variables specific to the controllable device. In one example, the controllable variables may include but are not limited to various types of color characteristics, intensity of light, tuning light, rate of air flow, humidity level, temperature range, open/close of the doors/windows etc. The memory 108 also stores instructions, which is accessible by the processor 110 such that execution of the instructions by the processor 110 to perform various functions described herein.

In one implementation, the processor 110 determines a communication capability among the plurality of communication capabilities of the controller based on the identifying data. The processor 110 functions to adapt at least one aspect of the control data signal based on the determined communication capability of the controller 112. In one example, the processor 110 adapts to a format of the command signal of the control data signal to match with the command signal protocol of the determined communication capability. In another implementation, the processor 110 determines a type of the controllable device 102 among the plurality of types of controllable devices based on the identifying data. In one implementation, the processor 110 adapts the control data signal to the determined type of the controllable device 102. In one example, the controllable device 102 is white LED luminaire that supports ON/OFF and dimming functions, thus the processor 110 adapts the control data signal associated with the control instruction to turn the white LED luminaire ON/Off or dim the white LED luminaire. In another example, the controllable device 102 is a specific LED luminaire that supports a specific intensity variation (such as 10%, 20% etc.) among the several intensity variations of the dimming functions, thus the processor 110 adapts the control data signal associated with the control instructions to the specific intensity variation of the dimming function of the specific Led luminaire. In a further example, the controllable device 102 is a HVAC component that supports functions such as increase/decrease in temperature in the area, thus the processor 110 adapts the control data signal associated with the control instruction to increase or decrease the temperature in the area.

In one implementation, the processor 110 retrieves data identifying control operations supported by the controller based on the identifying data from the controller 112. As discussed above, the control operations supported by the controller may include light related control operations, building related control operations etc. Some of the light related control operations include turning lights on/off, dimming lights, color temperature, color red green blue, circadian rhythm, chaotic program etc. Building related control operations include heating/cooling & air control, door access controls, fire and safety control, on-premises surveillance control etc.

In one implementation, the memory 108 stores the user preference data associated with the premises 101 and the time t for the user ID. As discussed above, in one example, the user preference data includes one or more control instructions among the control instructions. In one implementation, upon receipt of the identifying data, the processor 110 accesses the memory 108 to retrieve the user preference data for the user associated with the controller 112. In one implementation, the processor 110 sends the user preference data to an output of the user device (not shown) of the user via the data communication transmitter 207. In one example the control instruction in the user preference data corresponds to a user selection of the one or more control operations (corresponding to the control data signal) among the identified control operations supported by the controller 112.

Figure 3:
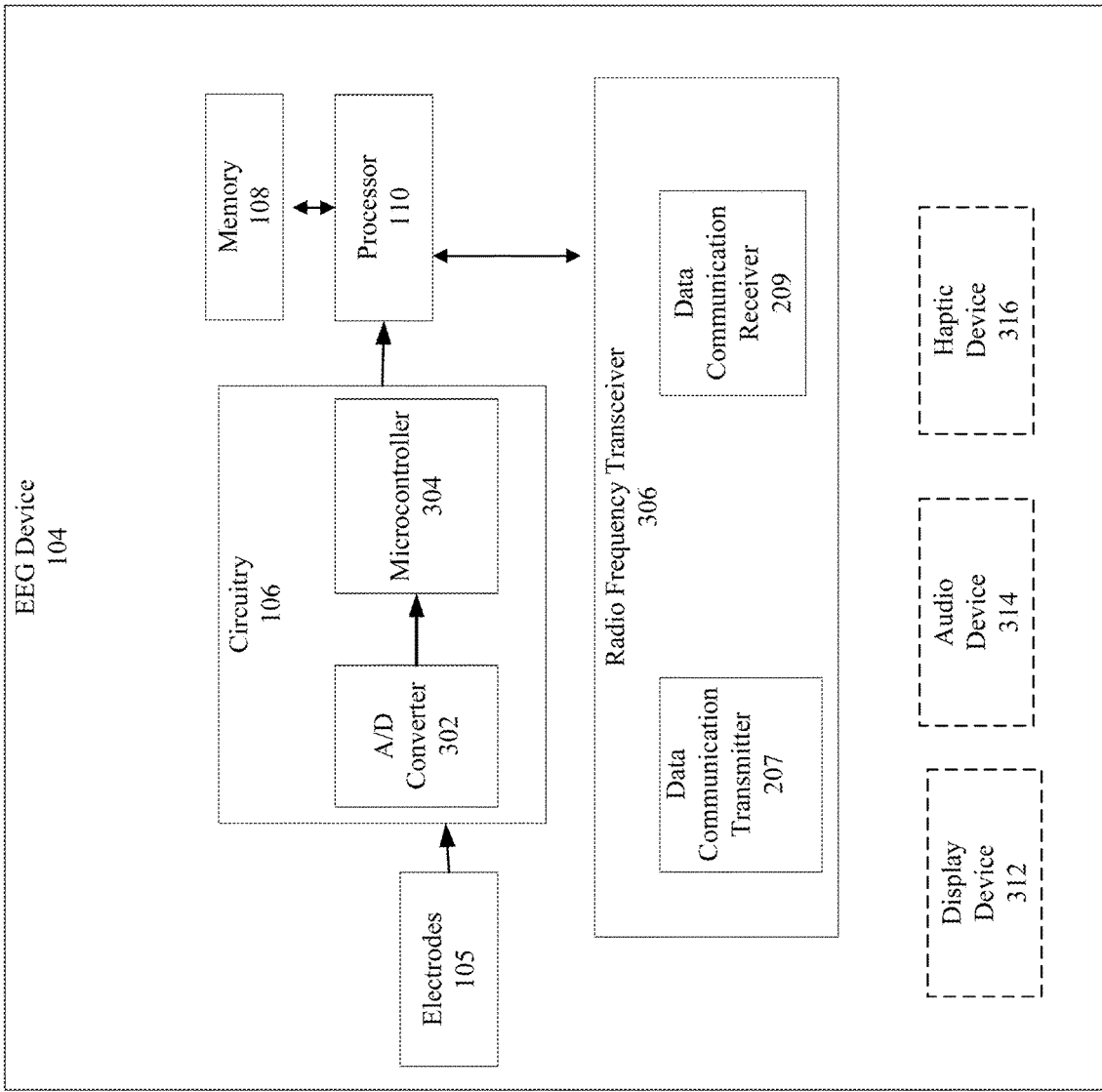
FIG. 3 is a functional block diagram example of an EEG device for control of a premises related service in a premises.

FIG. 3 illustrates is a functional block diagram example of the EEG device of FIG. 1 for control of a premises related service in a premises 101. In this example, besides the electrodes 105, the EEG device 104 also includes the circuitry 106, the memory 108 and the processor 110. As shown, the circuitry 106 includes an analog to digital (A/D) converter 302 and a microcontroller 304. As discussed above, the circuitry 106 processes the EEG signals detected by the electrodes 105. The EEG signals detected by the electrodes 105 are analog signals. In one example, A/D converter 302 converts the analog signals into digital signals and the microcontroller 304 microcontroller 304 assembles the digital signals outputted from the A/D converter 302 into a format for a transmission to the processor 110.

The EEG device 104 includes a radio frequency (RF) transceiver 306 coupled to the processor 110. The RF transceiver 306 includes the data communication transmitter 207 and the data communication receiver 209. The data communication receiver 209 receives data over the RF spectrum. The data communication transmitter 207 transmits the received data over the RF spectrum to a user device (e.g. display device 312, audio device 314, and haptic device 316) of the user integrated in the EEG device. As discussed above, the memory 108 stores user the user ID uniquely associated with the EEG device 104 identifying a user among a plurality of users of the EEG device 104 in the premises 101. Also, as discussed above, the memory 108 stores one or more control instructions. The processor 110 is coupled to the circuitry 106 and during configuration phase, configures the EEG device 104 to receive the data regarding the detected EEG signals and determines a control instruction among the plurality of control instructions associated with the EEG signals. Also, during the configuration phase, the processor 110 stores for the user ID in the memory 108, the determined control instruction in associated with the location ID of the premises 101 and the respective time t. Also, as discussed above, during the operational phase, in the premises 101, at the later respective time t, the processor 110 determines the user ID of the EEG device 104 and based on the detected EEG signals, accesses the user preference data to retrieve the control instruction and generate the control data signal corresponding to the control instruction. As discussed above, the control data signal corresponds to a control of an operation of the controllable device, which provides a premises related service in the premises 101. Also, as discussed above, during the operational phase, the processor 110 determines another control instruction among the plurality of control instructions based on continued detection of the EEG signals and thus updates the user preference data by replacing the control instruction with another control instruction. Other control instruction is different from the control instruction. Further, as discussed above, during the operational phase, the processor 110 generates another control data signal corresponding to other control operation among the plurality of operations. Other control operation is different from the control operation.

As discussed above, in one implementation, the memory 108 stores the user ID uniquely associated with the EEG device 104 identifying a user among a plurality of users of the EEG device 104 in the premises 101. Also discussed above, in one implementation, the memory 108 also stores a plurality of hierarchical classes/levels of user(s) as member(s) with each level having permissions to use one or more control instructions among the plurality of control instructions. In one implementation, the data communication receiver 209 receives a user identification data of the EEG device 104. As discussed above, the processor 110 utilizes the received user identification data to search the memory 108 to identify the user among the plurality of users and the corresponding hierarchy level of the identified user of which the user is the member. The processor 110 transmits the control data signal to the controller 112 that relates to the one or more control instructions permitted for the corresponding hierarchy level.

As discussed above, in one implementation, the data communication receiver 209 receives identifying data from the controller 112. Also, as discussed above, the identifying data includes but is not limited to location of the controller in the area, communication capabilities of the controller, control operations supported by the controller, types of controllable devices controlled by the controller, controller variables for each type of controllable device, or combinations thereof.

As discussed above, in one implementation, the processor 110 determines a communication capability among the plurality of communication capabilities of the controller based on the identifying data. The processor 110 functions to adapt at least one aspect of the control data signal based on the determined communication capability of the controller 112. Also, as discussed above, in another implementation, the processor 110 determines a type of the controllable device 102 among the plurality of types of controllable devices based on the identifying data. In one implementation, the processor 110 adapts the control data signal to the determined type of the controllable device 102.

As discussed above, in one implementation, the processor 110 retrieves data identifying control operations supported by the controller based on the identifying data from the controller 112. The processor 110 sends the data identifying control operations to an output device (e, g, display device 312, audio device 314 and haptic device 316) of the user via the data communication transmitter 207. In one example, the control instruction corresponds to a user selection of a control operation among the identified control operations supported by the controller 112.

As discussed above, in one implementation, upon receipt of the identifying data, the processor 110 accesses the memory 108 to retrieve the user preference data for the user associated with the controller 112. The processor 110 sends the user preference data to an output device (e.g. display device 312, audio device 314 and the haptic device 316) of the user device via the data communication transmitter 207. In one example the control instruction corresponds to the user preference data including the preferred user selection of the one or more control operations among the identified control operations supported by the controller 112.

Figure 4:
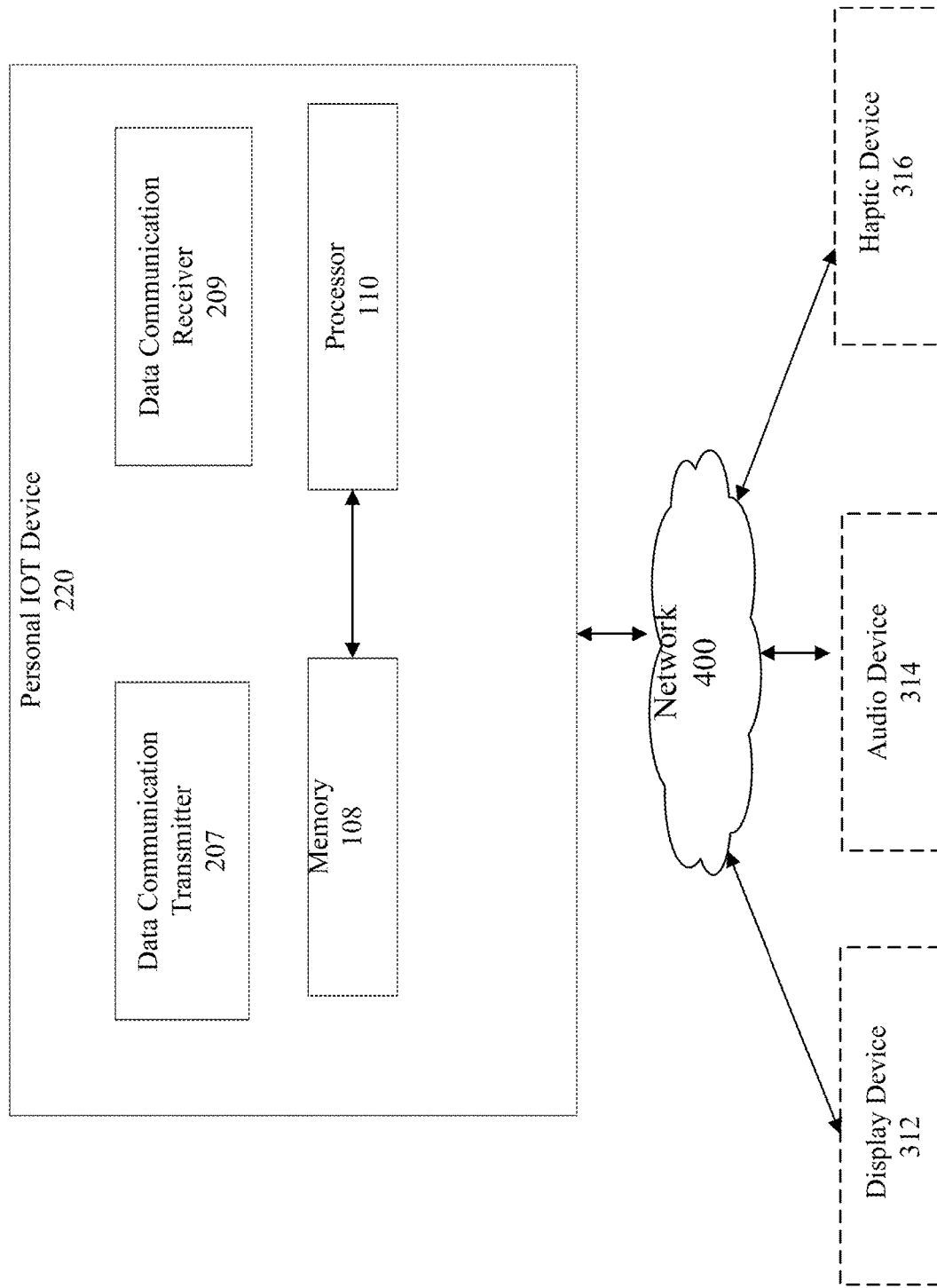
FIG. 4 is a functional block diagram of an example of a personal Internet of Things (PIOT) device for EEG based control of a premises related service in a premises.

FIG. 4 illustrates functional block diagram of an example of a personal Internet of Things (PIOT) device of FIG. 2 for EEG based control of a premises related service in a premises, for example the premises 101. As illustrated, the PIOT device 220 includes the memory 108 and the processor 110, the data communication transmitter 207 and the data communication receiver 209. In one implementation, the data communication receiver 209 receives data over the RF spectrum. In one implementation, the data communication transmitter 207 transmits the received data over the RF spectrum to a user device (e.g. display device 312, audio device 314, and haptic device 316). The data communication transmitter 207 transmits the received data to the user device via a network 400 as shown in FIG. 4. In one example, the network 400 is a RF wireless communication network.

As discussed above, in one example, the memory 108 stores user the user ID uniquely associated with the PIOT device 220 identifying a user among a plurality of users in the premises 101. Also, as discussed above, the memory 108 stores one or more control instructions. In one implementation, the processor 110 is coupled to the data communication receiver 209 and thus also configures the PIOT device 220 to receive the data regarding the detected signals (EEG or nerve signals) and determines a control instruction among the plurality of control instructions associated with the EEG signals. Also, during the configuration phase, the processor 110 stores for the user ID in the memory 108, the determined control instruction in associated with the location ID of the premises 101 and the respective time t. Also, as discussed above, during the operational phase, in the premises 101, at the later respective time t, the processor 110 determines the user ID of the EEG device 104 and based on the detected EEG signals, accesses the user preference data to retrieve the control instruction and generate the control data signal corresponding to the control instruction. As discussed above, the control data signal corresponds to a control of an operation of the controllable device, which provides a premises related service in the premises 101. Also, as discussed above, during the operational phase, the processor 110 determines another control instruction among the plurality of control instructions based on continued detection of the EEG signals and thus updates the user preference data by replacing the control instruction with another control instruction. Other control instruction is different from the control instruction. Further, as discussed above, during the operational phase, the processor 110 generates another control data signal corresponding to other control operation among the plurality of operations. Other control operation is different from the control operation.

As discussed above, in one implementation, the memory 108 stores the user ID uniquely associated with the PIOT device 220 identifying a user among a plurality of users of the PIOT device 220 in the area 101 of the premises. Also discussed above, in one implementation, the memory 108 also stores a plurality of hierarchical classes/levels of user(s) as member(s) with each class having permissions to use one or more control instructions among the plurality of control instructions. In one implementation, the data communication receiver 209 receives a user identification data of the PIOT device 220. As discussed above, the processor 110 utilizes the received user identification data to search the memory 108 to identify the user among the plurality of users and the corresponding hierarchy level of the identified user of which the user is the member. The processor 110 transmits the control data signal to the controller 112 that relates to the one or more control instructions permitted for the corresponding hierarchy level.

As discussed above, in one implementation, the data communication receiver 209 receives identifying data from the controller 112. Also, as discussed above, the identifying data includes but is not limited to location of the controller in the area, communication capabilities of the controller, control operations supported by the controller, types of controllable devices controlled by the controller, controller variables for each type of controllable device, or combinations thereof.

As discussed above, in one implementation, the processor 110 determines a communication capability among the plurality of communication capabilities of the controller based on the identifying data. The processor 110 functions to adapt at least one aspect of the control data signal based on the determined communication capability of the controller 112. Also, as discussed above, in another implementation, the processor 110 determines a type of the controllable device 102 among the plurality of types of controllable devices based on the identifying data. In one implementation, the processor 110 adapts the control data signal to the determined type of the controllable device 102.

As discussed above, in one implementation, the processor 110 retrieves data identifying control operations supported by the controller based on the identifying data from the controller 112. The processor 110 sends the data identifying control operations to an output device (e, g, display device 312, audio device 314 and haptic device 316) of the user via the data communication transmitter 207. In one example, the control instruction corresponds to a user selection of a control operation among the identified control operations supported by the controller 112.

As discussed above, in one implementation, upon receipt of the identifying data, the processor 110 accesses the memory 108 to retrieve the user preference data for the user associated with the controller 112. The processor 110 sends the user preference data to an output device (e.g. display device 312, audio device 314 and the haptic device 316) of the user device via the data communication transmitter 207. In one example the control instruction corresponds to the user preference data including the preferred user selection of the one or more control operations among the identified control operations supported by the controller 112.

FIG. 5 illustrates an example flowchart of a method 500 for system level configuration of an EEG based system for controlling a premises related service provided by a controllable device in an area of a premises. In one implementation, the method 500 is performed by the processor 110 of FIG. 1 during the configuration phase.

At block 502, detect signals (EEG signals) from an EEG device at a respective time among a plurality of times in a respective premises among a plurality of premises. In one implementation, the EEG signals are detected in a premises including a premises related service provided by a controllable device. In one implementation, the controllable device includes one of a luminaire or a building automation control (BAC) appliance. As discussed above, in one implementation, the EEG device is configured to be positioned on a head of a user and the detected signals are signals detected from a brain of the user. At block 504, obtain an identification (ID) associated with the premises at the time. At block 506, determine a control instruction associated with the EEG signals detected from among a plurality of control instructions. At block 508, store, in a memory, the determined control instruction in association with the obtained premises ID, as a user preference data relative to the respective premises for a user of the EEG device, for communication to a controllable device at the respective premises at a later time during an operational phase based at least in part on similar EEG signals detected via the one or more electrodes of the EEG device and receiving the premises ID at the respective time. At block 510, at a later time, during an operational phase at the respective location, utilize the stored user preference data to communicate a control data signal corresponding to the determined control instruction to a controllable device at the respective premises based at least in part on similar EEG signals detected at the later time via the one or more electrodes of the EEG device and reception of the premises ID at the respective premises.

Figure 5A:
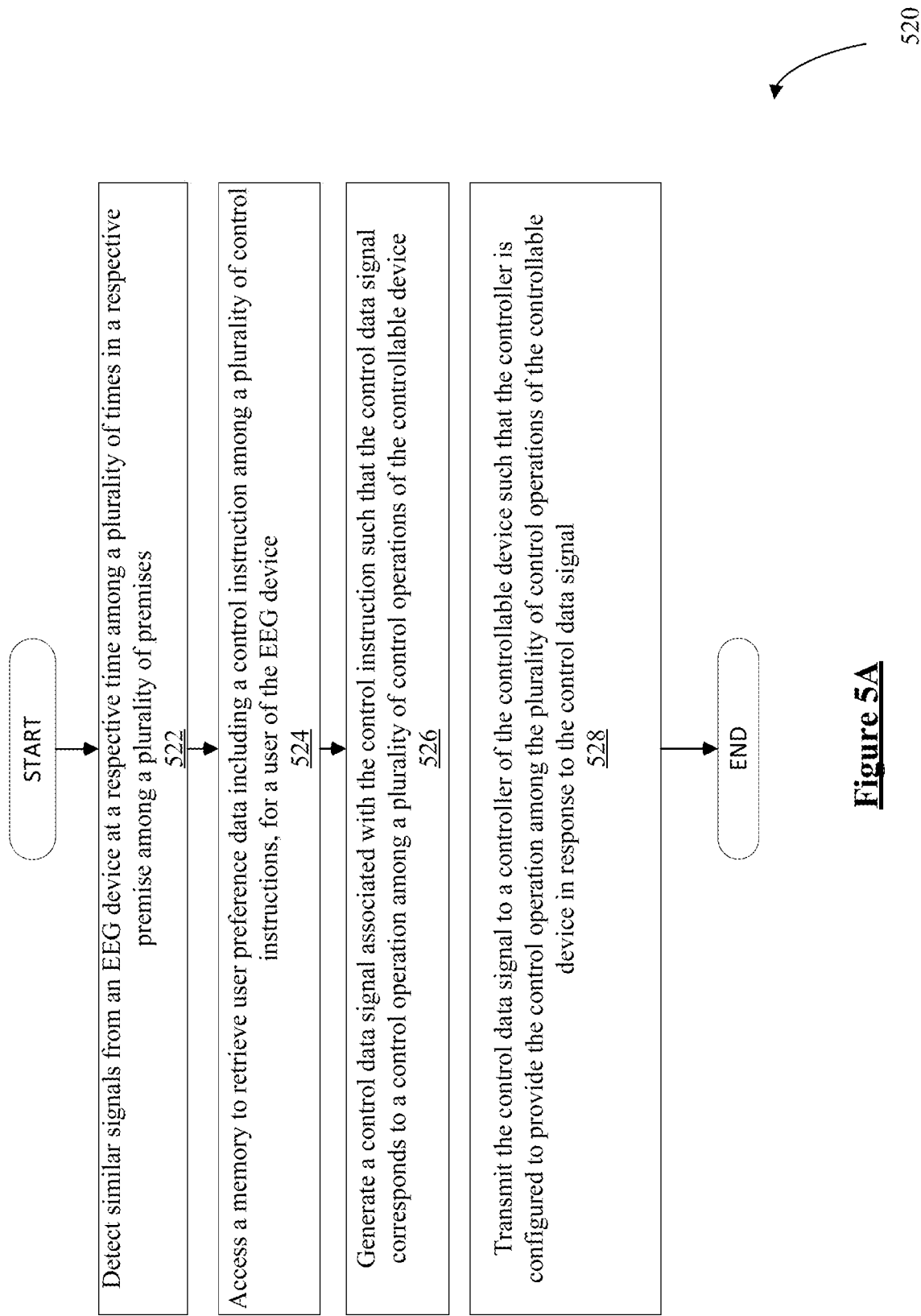
FIG. 5A is another example flowchart illustrating a method for a system level real-time operational phase of an EEG based control system based on the configuration of the EEG system.

FIG. 5A illustrates another example of a flowchart of a method 520 for a system level real-time operational phase of an EEG based control system based on the configuration of the EEG system. In one implementation, the method 520 is performed by the processor 110 of FIG. 1 during the real-time operational phase.

At block 522, detect similar EEG signals from an EEG device at a respective time among a plurality of times in a respective premises among a plurality of premises. At block 524 access a memory to retrieve a user preference data, including a control instruction among a plurality of control instructions, for a user of the EEG device. At 526, generate a control data signal associated with the control instruction such that the control data signal corresponds to a control operation among a plurality of control operations of the controllable device. At 528, transmit the control data signal to a controller of the controllable device such that the controller is configured to provide the control operation among the plurality of control operations of the controllable device in response to the control data signal.

Figure 5B:
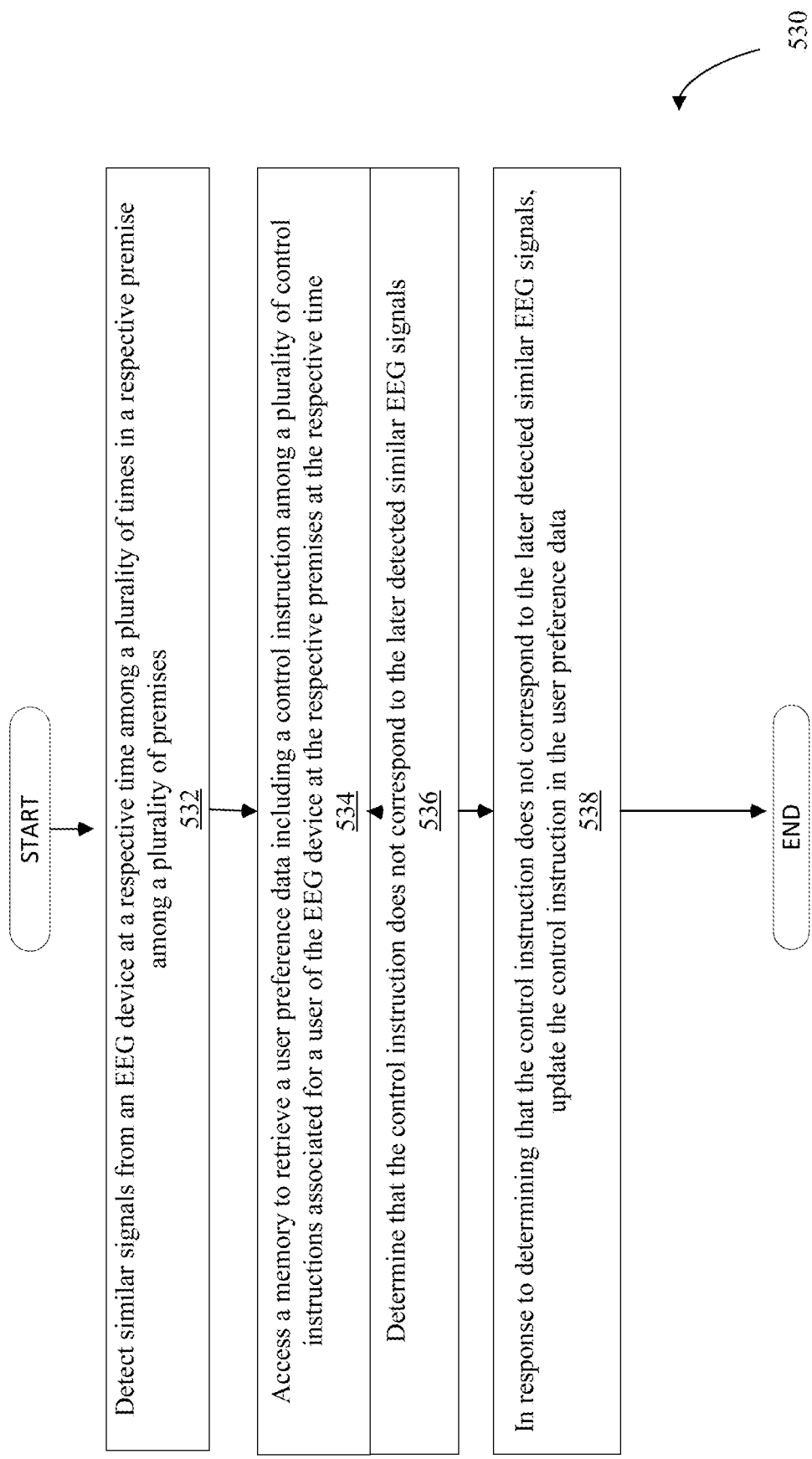
FIG. 5B is a further example flowchart illustrating a method for system level real-time operation of an EEG based control system based on the configuration of the EEG system.

FIG. 5B illustrates a further example of a flowchart of a method 530 for system level real-time operation of an EEG based control system based on the configuration of the EEG system. In one implementation, the method 530 is performed by the processor 110 of FIG. 1 during the real-time operational phase.

At block 532, detect similar signals from an EEG device at a respective time among a plurality of times in a respective premise among a plurality of premises. At block 534. access a memory to retrieve a user preference data, including a control instruction among a plurality of control instructions, for a user of the EEG device at the respective premises at the respective time. At block 536, determine that the control instruction does not correspond to the later detected similar EEG signals. At block 538, in response to determining that the control instruction does not correspond to the later detected similar EEG signals, update the control instruction in the user preference data.

Figure 6:
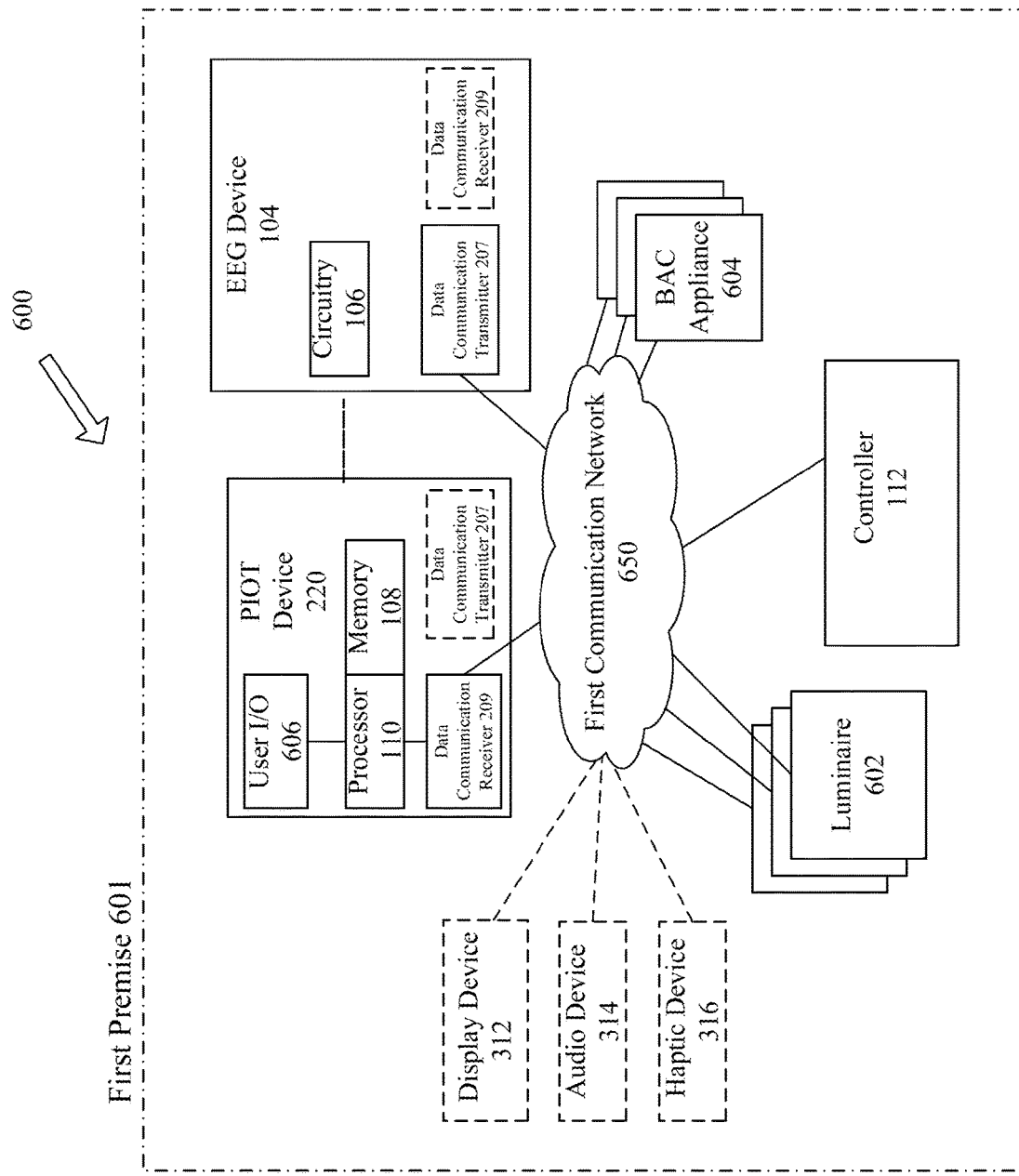
FIG. 6 is a functional block diagram of an example of a system of lighting related equipment and building automation control (BAC) capable appliances as well as one or more computer elements that may support real-time operation of EEG control of the lighting related equipment and the BAC capable appliance.

As discussed above, the controllable device 102 provides a premises related service in an area 101 of a premises. The controllable device 102 may include luminaire, various BAC appliances etc. FIG. 6 is a functional block diagram of an example of a system 600 of lighting related equipment and building automation control (BAC) capable appliances as well as one or more computer elements that may support real-time operation of EEG control of the lighting related equipment and the BAC capable appliance serving a first premises represented by a first premises 601. The first premises 601 includes a luminaire 602 and a BAC appliance 604 both of which represent the controllable device 102. The luminaire 602 is configured to provide a desired level of lighting for the intended use of the particular space in the room 601 and the BAC appliance 604 is configured for instance, regulate the temperature in the room 601 or control access to the first premises, etc. Although, FIG. 6 illustrates providing lighting control and building management services in the first premises 601, it is known to one of ordinary skill in the art that such services are provided in a similar manner in other rooms and/or other types of services areas within or on a particular area of the premises such as in a building or indoors and outdoors about a campus or the like. Also, even though, a single luminaire and a single BAC appliance is illustrated in the first premises 601, one of ordinary skill in the art would appreciate that the first premises 601 may include multiple luminaires and multiple BAC appliances.

In one implementation, the first premises 601 includes the controller 112 as a separate standalone system component, although, the controller 112 may be included in the luminaire 602 and the BAC appliance 604. The controller 112 is configured to control the premises related services in the first premises 601. In one implementation such premises related services include lighting operations, of the system such as occupancy, ambient light level or color characteristics of light in the area or level or color of light emitted from the luminaire 602 serving the particular portion of the area. In another implementation, such premises related services include operations relevant to building management functions of the system or for more general communication about conditions in the area for still further purposes. Examples of other operations include temperature or humidity for HVAC control, vibration for reporting of earthquakes or similar events, fire, smoke or gas detection, sound for user input or for detection of breakage or the like, as well as window or door state for security or access control. Other examples of operations include power monitoring, an object/occupant identification, etc.

In one implementation, the controller 112 is coupled to communicate with the controllable device 102 such as the luminaire 602 and the BAC appliance 604 via a first communication network 650 such as optical, radio frequency wireless or wired communication. In one example, the premises related service is the light related operations. The controller 112 is configured to control the light related operations associated with the luminaire 602. In another example, the premises related service is the building management functions. In another example, the controller 112 is configured to control the building management functions associated with the BAC appliance 604. In one implementation, a user (not shown) with EEG device 104 including the circuitry 106 and the data communication transmitter 207 is configured to be positioned on a head of the user is in the first premises 601. In one example, the EEG device 104 detects EEG signals from the brain of the user, which are processed by the circuitry 106 and transmitted by the data communication transmitter 207 to the PIOT device 220 of the user. The EEG device 104 may also include the data communication receiver 209 as shown. The PIOT device 220 may also include the data communication transmitter as shown. In one implementation, the EEG device 104 and the PIOT device 220 communicate with each other via the first communication network 650. In an alternate implementation, the EEG device 104 and the PIOT device 220 directly communicate with each other, for example, via a wire or fiber link. In another alternate implementation, the PIOT device 220 is coupled to communicate with one or more of the user devices (e.g. display device 312, audio device 314 and haptic device 316).

In one implementation, as discussed above during the configuration phase, the processor 110 utilizes the instructions in the memory 108 to execute functions such as obtain an identification associated with the first premises 101 at a time among a plurality of times; determine a control instruction associated with the EEG signals detected via the one or more electrodes of the EEG device, from among a plurality of control instructions stored in the memory 108; and store the determined control instruction in association with the obtained location identification and the respective time, as a user preference data relative to the first premises 101 at the respective time, for communication to one of the luminaire 602 or the BAC appliance 604. In one implementation, during the real-time operational phase, the processor 110 utilizes the program instructions in the memory 108 to access the memory 108 to retrieve user preference data based on similarly detected EEG signals at the later time in the first premises 101, generates a control data signal associated with the control instruction such that the control data signal corresponds to a control operation among a plurality of control operations of one of the luminaire 602 or the BAC appliance 604, and transmit the control data signal to the controller 112. The data communication receiver 209 transmits the control data signal to the controller 112 to control the premises related service provided by one of the luminaire 602 and/or the BAC appliance 604 in the first premises 601. In one example, the controller 112 is configured to provide the control operation among the plurality of control operations of one of the luminaire 602 or the BAC appliance 604 in response to the control data signal.

In another implementation, as discussed above, during the real-time operational phase, the processor 110, access the memory 108 to retrieve a user preference data including a control instruction among a plurality of control instructions associated with a user ID of the EEG device at the first premise 101, determine that the detected EEG signals for the user ID do not correspond to the control instruction associated with the location ID in the first premise 601, analyze the detected EEG signals to determine that the detected EEG signals correspond to another control instruction among the plurality of control instructions stored in the memory 108 and update the associated control instruction with other control instruction as the user preference data relative to the premises 101. In another implementation, the processor 110 utilizes the program instructions in the memory 108 to generate another control data signal based on another control instruction. The data communication receiver 209 transmits another control data signal to the controller 112 to control the premises related service provided by one of the luminaire 602 and/or the BAC appliance 604 in the room 601. In one example, the EEG device 104 and the PIOT device 220 includes a user interface (UI) 606 to communicate with the user device such as the display device 312, audio device 314 and haptic device 316. Some examples of the UI 606 includes toggle switch, one or more push button switches, a rotary controller, one or more sliders, a keypad, various indicator lights, haptic feedback components, and/or a touchscreen display, Other examples of the UI may include a video input and associated processing for gestural control detection, a microphone, an occupancy/motion sensor, proximity sensor, etc. Although not shown, each of the system elements that uses power to operate as described will include a power supply circuit and will connect to or possibly contain a power source.

Although the EEG device, PIOT device and any optional output devices for providing feedback or other information to the user may be separated, in most examples, such devices will be carried or worn by the user at any one time, whether on or off of the premises where the controllable device is located.

Figure 6A:
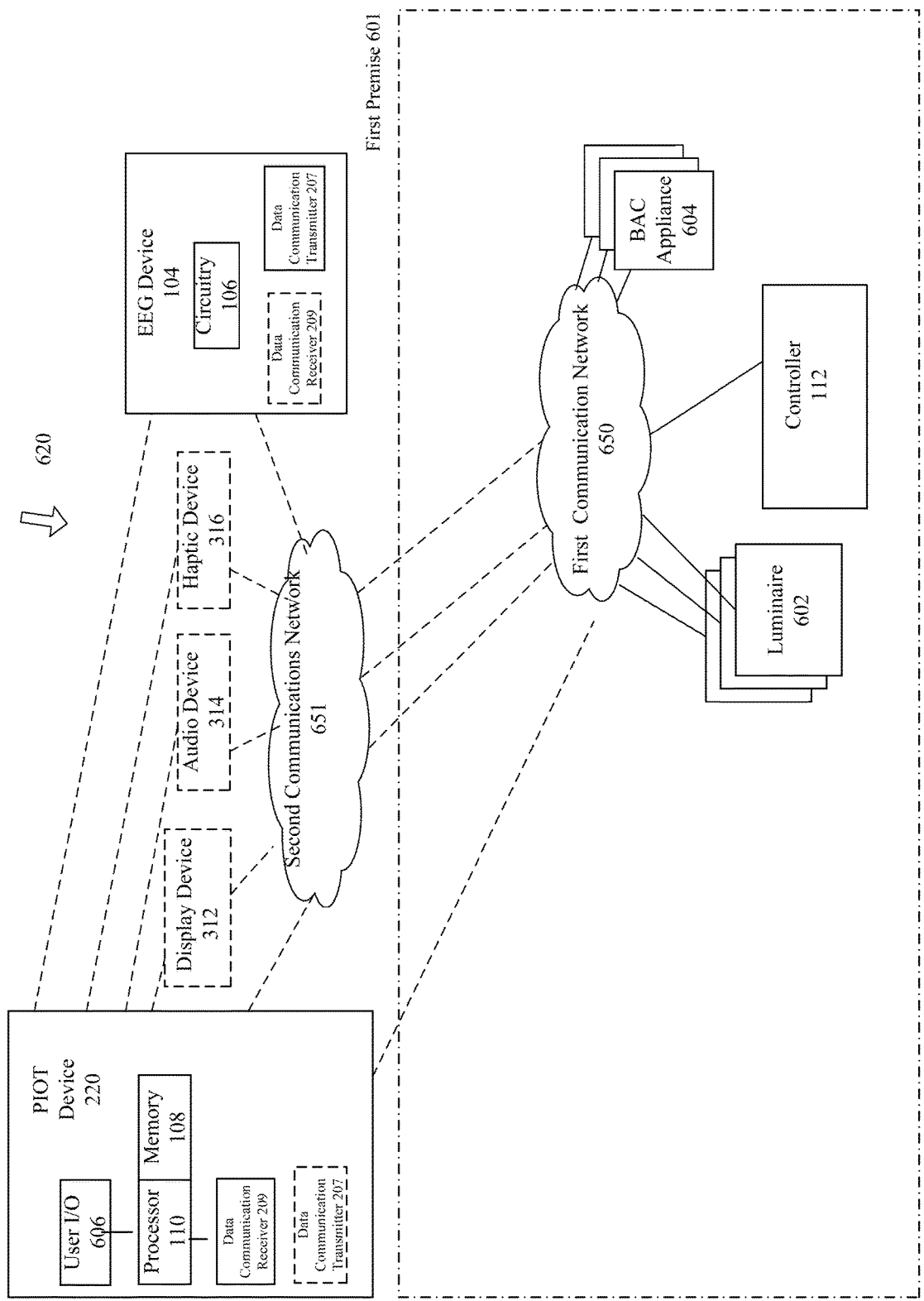
FIG. 6A is a functional block diagram of another example of lighting related equipment and building automation control (BAC) capable appliances as well as one or more computer elements that may support real-time operation of EEG control of the lighting related equipment and the BAC capable appliance.

FIG. 6A illustrates functional block diagram of another example of a system 620 including lighting related equipment and building automation control (BAC) capable appliances as well as one or more computer elements that may support real-time operation of EEG control of the lighting related equipment and the BAC capable appliance. The system 620 functions similar to the system 600 of FIG. 6A as discussed above except the EEG device 104 and the PIOT device 220 are located outside the first premises 601 such that the EEG signals are detected by the EEG device 104 outside of the premises of the first premises 601, which are then processed by the circuitry 106 and transmitted by the data communication transmitter 207 to the PIOT device 220. The PIOT device 220 is shown by way of example outside of the premises and/or possibly outside of the room 601, e.g. where the EEG device 104 and the PIOT device 220 are worn and/or carried by the user. The PIOT device 220, however, may be inside the room and/or the premises (e.g. at the same or another location as the EEG device 104). In one example, the user devices such as the display device 312, audio device 314 and haptic device 316 are also located outside the premises of the room 601, e.g. with the user wearing the EEG device 104; and the EEG device 104 and the PIOT device 220 device communicate with each other and with such user devices via a second communication network 651 such as an optical, RF wireless or a wired communication network.

Figure 6B:
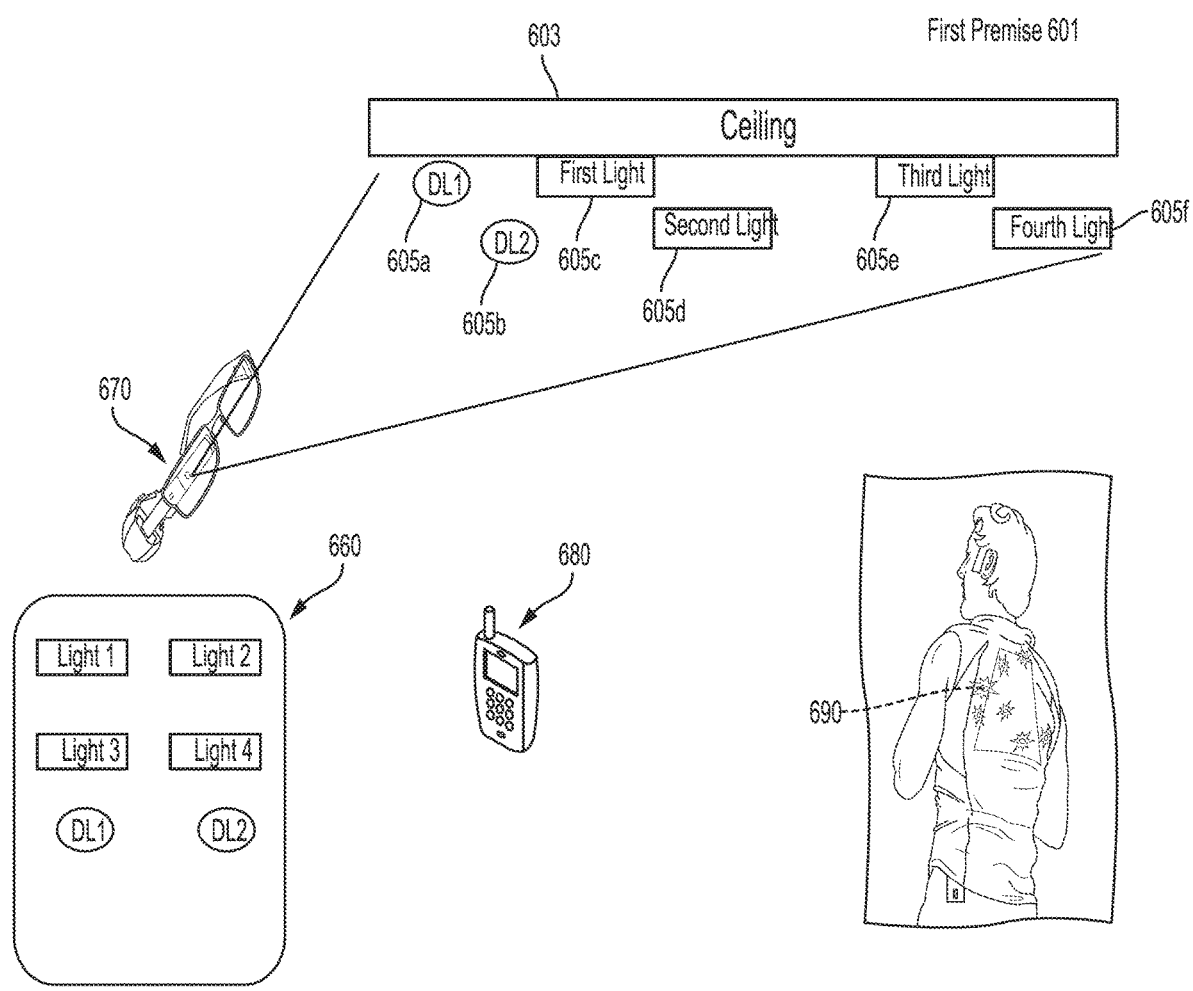
FIG. 6B illustrates an example of providing data associated with the lighting devices in an area of premises.

FIG. 6B illustrates an example of providing data associated with the lighting device as the controllable device 102 in the first premises 601. Also, shown is a ceiling 603 in the room 601 luminaires or the like labeled as "lights" for convenience in the drawing. In one example, there are illustrated six lighting devices, two downlights, a first ($1^{st}$) downlight (DL1) 605a a second ($2^{nd}$) downlight (DL2) .605b, and four lights, a first light 605c, a second light 605d, a third light 605e, and a fourth light 605f. In one example, the four lights 605c-605f are mounted on or hung below the ceiling 603. In one example, the two downlights, 605a and 605b are downlight type fixtures that may be recessed into, mounted or hung below the ceiling 603. Although the light sources are illustrated to be located on the ceiling 603, it should be apparent that the light sources may be located either wall or floor or combinations thereof in the first premises 601. Also, in the example, six lighting devices are shown, it is known to one of ordinary skill in the art that less than or more than six lighting devices may be provided in the first premises 601. The lighting devices may include but not limited to light emitting diodes (LEDs), fluorescent lamps, halogen lamps, metal halide lamps, high intensity discharge lamps or like.

In one implementation, the data associated with the six lighting devices is provided to the user via one of the user devices such as the display device 312, audio device 314 and the haptic device 316. In one example the data is provided to the user upon request from the user when the user enters the room 601. In another example, the data is automatically provided to the user when the user enters the room 601. In one example, the display device 312 is a smartphone 660 and the data may be displayed on a screen of the smartphone 660 as shown. In another example, the display device is a head gear 670 including a camera (not shown) and the data may be displayed to the user who wears the head gear 313. In one example, the head gear 670 are augmented reality (AR) glasses, which includes additional hardware such as an optical sensor/camera (not shown) to track the eyeball of the wearer of the AR glasses and estimates gaze so that EEG commands to control the lights can be directed to specific lights being looked at by the wearer of the AR glasses. Other administrator level functions such as grouping lights can also be performed, highly augmented by the visual feedback to the AR glasses. In one example, the audio device 314 is a standard phone 680 and the data is provided to the user via audio on the standard phone 680. In one example, the haptic device 316 is a wearable device 690, which provides for a physical contact between the user and a computer such as the user will receive the data via felt sensation on some part of the body. In one example, upon user selection of the data (associated with the lighting devices as shown) as provided to the user, user selections are collected and stored as the user preference data. As discussed above, the user preference data is preferred user selection of one or more control operations among the identified control operations of the controllable device 102 supported by the controllable 112.

Figure 6C:
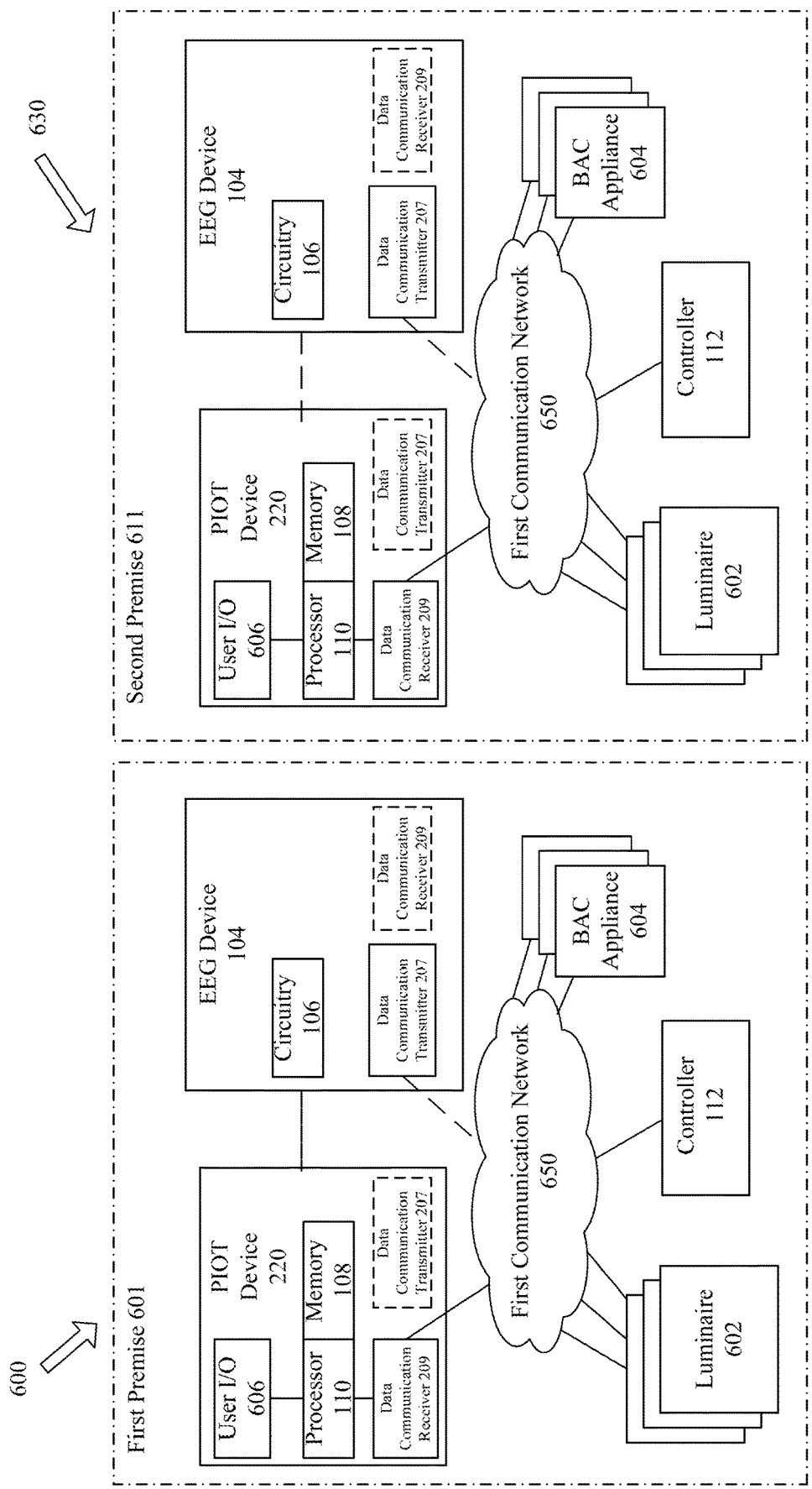
FIG. 6C is a functional block diagram of another example of lighting related equipment and building automation control (BAC) capable appliances as well as one or more computer elements that may support real-time operation of EEG control of the lighting related equipment and the BAC capable appliance, for example, which may provide different user preferences at different premises.

FIG. 6C illustrates a functional block diagram of another example of lighting related equipment and building automation control (BAC) capable appliances as well as one or more computer elements that may support real-time operation of EEG control of the lighting related equipment and the BAC capable appliance, for example, which may provide different user preferences at different premises, for example, the second premise 611. In one example, the system 630 is different from the system 600 although includes the same components of the system 600. In one implementation, during the configuration phase, the processor 110 in the second premises 611 functions similarly to the processor 110 in the first premises 601 as discussed above in FIG. 6. In one implementation, during the configuration phase, the processor 110 in the second premises 611 obtains an identification associated with the second premises 101 at a time among a plurality of times, determines a control instruction associated with the EEG signals detected via the one or more electrodes of the EEG device 104, from among a plurality of control instructions stored in the memory 108 of the second premises 611 and stores the determined control instruction in association with the obtained location identification of the second premises 611 and the respective time, as a user preference data relative to the second premises 611 at the respective time, for communication to one of the luminaire 602 or the BAC appliance 604 in the second premises 611. In one example, the user preference data stored in the memory 108 of the second premises 611 is same as the user preference data stored in the memory 108 of the first premises 601. In another example, the user preference data stored in the memory 108 of the second premises 611 is different from the user preference data stored in the memory 108 of the first premises 601.

In one implementation, during the real-time operational phase in the second premises 611, the processor 111 access the memory 108 to retrieve user preference data based on similarly detected EEG signals at the later time in the second premises 611, generates a control data signal associated with the control instruction such that the control data signal corresponds to a control operation among a plurality of control operations of one of the luminaire 602 or the BAC appliance 604 in the second premise 611, and transmits the control data signal to the controller 112 in the second premise 611. In another implementation, during the real-time operational phase in the second premises 611, the processor 110, access the memory 108 to retrieve a user preference data including a control instruction among a plurality of control instructions associated with a user ID of the EEG device at the second premises 611, determine that the detected EEG signals for the user ID do not correspond to the control instruction associated with the location ID in the second premises 611, analyze the detected EEG signals to determine that the detected EEG signals correspond to another control instruction among the plurality of control instructions stored in the memory 108 and update the associated control instruction with other control instruction as the user preference data of the second premises 611. In another implementation, the processor 110 utilizes the program instructions in the memory 108 to generate another control data signal based on another control instruction. In one implementation, the updated user preference data stored in the memory 108 of the second premises 611 is same as the updated user preference data stored in the memory 108 of the first premises 601. In another implementation, the updated user preference data stored in the memory 108 of the second premises 611 is different from the updated user preference data stored in the memory 108 of the first premise 601.

Figure 6D:
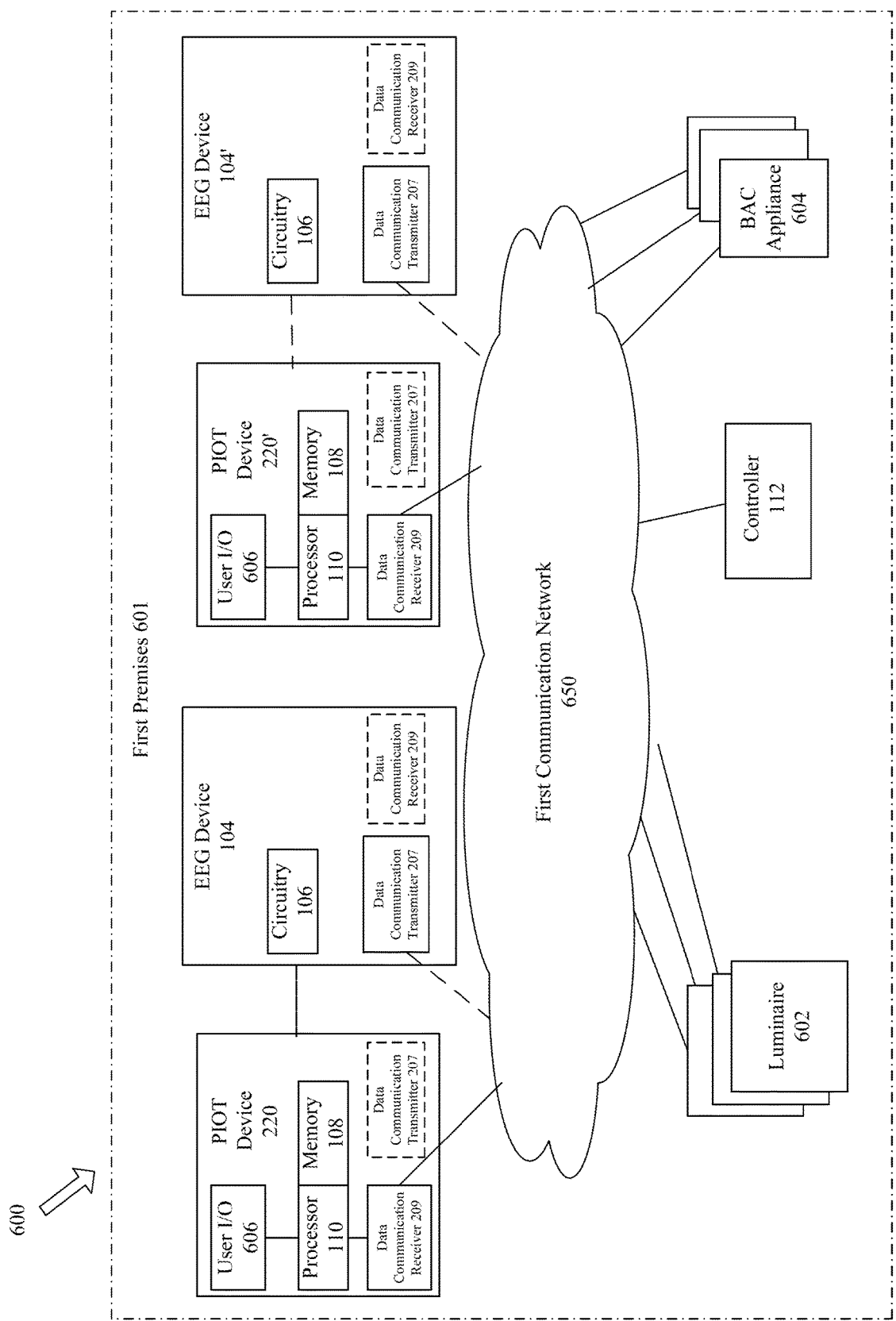
FIG. 6D is a functional block diagram of another example of lighting related equipment and building automation control (BAC) capable appliances as well as one or more computer elements that may support real-time operation of EEG control of the lighting related equipment and the BAC capable appliance, for example, which may support a hierarchy of different permissions or privilege levels for system users at a premises.

FIG. 6D is a functional block diagram of another example of lighting related equipment and building automation control (BAC) capable appliances as well as one or more computer elements that may support real-time operation of EEG control of the lighting related equipment and the BAC capable appliance, for example, which may support a hierarchy of different permissions or privilege levels for system users at a premises. As illustrated is another EEG device 104' and another PIOT device 220' that are associated with a user different from the user of the EEG device 104 and the PIOT device 220. As such the user ID of other EEG device 104' and/or other PIOT device 220' is different from the user ID of the device 104 and/or the PIOT device 220 to differentiate between the two different users. In one example, the memory 108 of other PIOT device 220' stores the user ID associated with other EEG device 104'. In one implementation, the processor 110 of other PIOT device 220' determines another control instruction among the plurality of control instructions associated with the EEG signals detected via the one or more electrodes of other EEG device 104' and stores as the user preference data the determined another control instruction in association with the location ID of the premises 601 and the time among the plurality of times. Other control instruction is different from the control instruction. The processor 110 of other PIOT device 220' also generates another control data signal associated with another control instruction. Other control instruction corresponds to other control operation among the plurality of control operations. Other control operation is different from the control operation.

Figure 7:
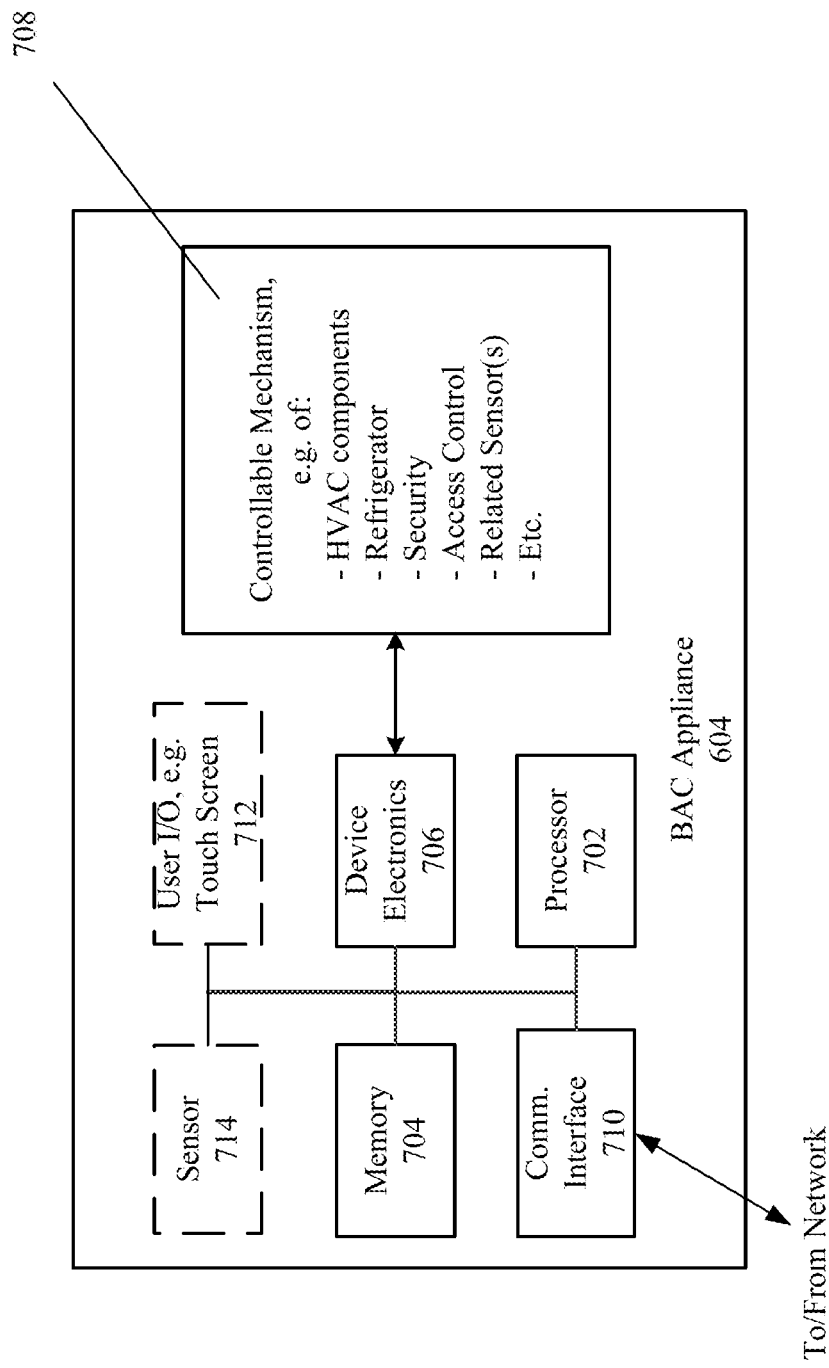
FIG. 7 is a functional block diagram of an example of an intelligent building automation control (BAC) capable appliance.

FIG. 7 illustrates functional block diagram of an example of an intelligent building management element, such as the BAC appliances 604 shown in FIG. 6. The BAC appliance 604 is an intelligent device in that the BAC appliance 604 includes a processor 702 and a memory 704 and program in the memory 704 for execution by the processor 702 to implement the intended functions of the BAC appliance 604. This 'brain' of the BAC appliance 604 will be coupled to and control appropriate device drive electronics 706. The drive electronics 706 provides an interface to a controllable mechanism 708 of the particular BAC appliance 604, to allow the processor 702 to control the mechanism, or to receive sensor data from the mechanism or both. The drive electronics 706 and the programming (e.g. stored in memory 704) that is run by the processor 702 to control operation of each particular BAC appliance 604 will depend on the particular type device used as the mechanism 708 and thus on the particular type of building management BAC appliance product it represents or implements.

The examples of BAC appliance 604 may be virtually any type of device, which may utilize data communications, in this case, via the elements and network of the system 600 of FIG. 6. By way of a few examples, the controllable mechanism 708 may be any of a variety of HVAC components (e.g. elements of a thermostat, one or more elements of the heat/cooling system, controllable vents or dampers within the duct work), one or more cooling or other elements of a refrigerator, any of a variety of components of a security system, any of a variety of access control elements, and/or sensors related to any or all of the above functions. The BAC appliance 604 also includes a communication interface 710. Similar to the communication interfaces in the other intelligent system elements (FIG. 6), the interface 710 connects or otherwise couples to the network in the service area and supports two-way data communication through the first communication network 650.

In the example of FIG. 7, although the BAC appliance 604 is shown as having one processor 702, it is known to one of ordinary skill in the art that the BAC appliance 604 may include multiple processors. For example, a particular configuration for a BAC appliance 604 may utilize a multi-core processor architecture. Also, some of the other components, such as the communications interfaces, may themselves include processors. Alternatively, the BAC appliance 604 may use a Micro-Control Unit (MCU), which is a microchip device (e.g. small computer or computer like device formed on a single chip) that incorporates a processor serving as the programmable central processing unit (CPU) as well as one or more of memories 704.

The BAC appliance 604 may include one or more input and/or output (I/O) elements 712 for a user interface (instead of or in addition to the mechanism 708). The user I/O element 712, for example, may include a toggle switch, a rotary controller, one or more sliders, a keypad and/or a touchscreen display. The precise user I/O element, if provided, depends on the operational characteristics of the particular BAC appliance 604. For example, for an HVAC controller, the user I/O element(s) 712 might be similar to those of a digital thermostat. A touchscreen display, as another example, may support touch and touch gesture input as well as visual display output. Other examples of the UI input may include a video input and associated processing for gestural control detection, a microphone, an occupancy/motion sensor, proximity sensor, etc. If provided, outputs may be visual, audible, tactile, etc. For example, a microphone and/or speaker may be used to support audible input and/or output, whereas a camera in combination with projector or display may be used to support visual input and/or output.

As an alternative or in addition to any sensors included in the controllable mechanism 708, the BAC appliance 604 may include one or more sensors 714 (instead of or in addition to the mechanism 401). If included, the type of sensor in a particular BAC appliance 604 would depend on the type of element and/or the mechanism 708 that the 'brain' controls either within the appliance itself or in same or another appliance via a BMS application 727 stored in the memory 704.

Figure 8:
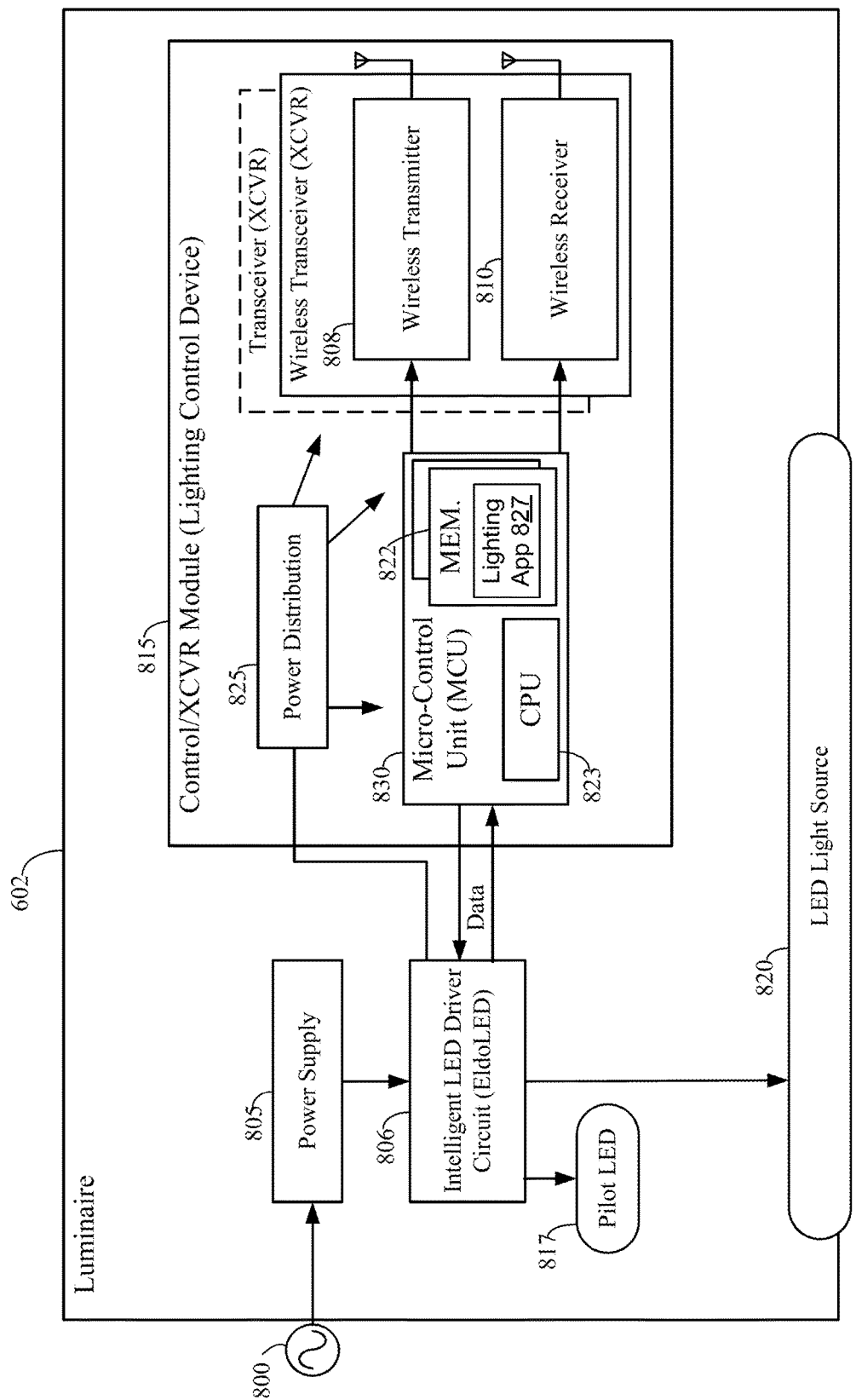
FIG. 8 is a functional block diagram of an example of an intelligent luminaire.

FIG. 8 illustrates a functional block diagram of an example of an intelligent luminaire, such as the luminaire 602 as shown in FIG. 6. Luminaire 602 is an integrated light fixture that generally includes a power supply 805 driven by a power source 800. Power supply 805 receives power from the power source 800, such as an AC mains, battery, solar panel, or any other AC or DC source. Power supply 805 may include a magnetic transformer, electronic transformer, switching converter, rectifier, or any other similar type of circuit to convert an input power signal into a power signal suitable for luminaire 602.

Luminaire 602 furthers include an intelligent LED driver circuit 806, control/XCVR module 815, and a light emitting diode (LED) light source 820. Intelligent LED driver circuit 806 is coupled to LED light source 820 and drives that LED light source 820 by regulating the power to LED light source 820 by providing a constant quantity or power to LED light source 320 as its electrical properties change with temperature, for example. The intelligent LED driver circuit 806 includes a driver circuit that provides power to LED light source 820 and a pilot LED 817. The pilot LED 817 may be included as part of the control/XCVR module 315. Intelligent LED driver circuit 806 may be a constant-voltage driver, constant-current driver, or AC LED driver type circuit that provides dimming through a pulse width modulation circuit and may have many channels for separate control of different LEDs or LED arrays. An example of a commercially available intelligent LED driver circuit 806 is manufactured by EldoLED. LED driver circuit 806 can further include an AC or DC current source or voltage source, a regulator, an amplifier (such as a linear amplifier or switching amplifier), a buck, boost, or buck/boost converter, or any other similar type of circuit or component. LED driver circuit 806 outputs a variable voltage or current to the LED light source 820 that may include a DC offset, such that its average value is nonzero, and/or an AC voltage.

Control/XCR module 815 includes power distribution circuitry 825 and a micro-control unit (MCU) 830. As shown, MCU 830 is coupled to LED driver circuit 806 and controls the light source operation of the LED light source 820. MCU 830 includes a memory 322 (volatile and non-volatile) and a central processing unit (CPU) 823. The memory 822 includes a lighting application 827 (which can be firmware) for both occupancy sensing/counting and lighting control operations. The power distribution circuitry 825 distributes power and ground voltages to the MCU 830, wireless transmitter 808 and wireless receiver 810, to provide reliable operation of the various circuitry on the sensor/processing circuitry chip.

Luminaire 602 also includes a wireless radio communication interface system configured for two way wireless communication on at least one band. Optionally, the wireless radio communication interface system may be a dual-band system. It should be understood that "dual-band" means communications over two separate RF bands. The communication over the two separate RF bands can occur simultaneously (concurrently); however, it should be understood that the communication over the two separate RF bands may not actually occur simultaneously.

In our example, the luminaire 602 has a radio set that includes radio transmitter 808 as well as a radio receiver 810, together forming a radio transceiver. The wireless transmitter 808 transmits RF signals on the lighting network. This wireless transmitter 808 wireless communication of control and systems operations information, during luminaire operation and during transmission over the first wireless communication band. The wireless receiver carries out receiving of the RF signals from other system elements on the network and generating RSSI data based on signal strengths of the received RF signals. If provided (optional) another transceiver (Tx and Rx) may be provided, for example, for point-to-point communication, over a second different wireless communication bands, e.g. for communication of information other than the control and systems operations information, concurrently with at least some communications over the first wireless communication band. Optionally, the luminaire 602 may have a radio set forming a second transceiver (shown in dotted lines, transmitter and receiver not separately shown). The included transceiver (solid lines), for example, may be a sub GHz transceiver or a Bluetooth transceiver configured to operate in a standard GHz band. A dual-band implementation might include two transceivers for different bands, e.g. for a sub GHz band and a GHz band for Bluetooth or the like. Additional transceivers may be provided. The particular bands/transceivers are described here by way of non-limiting example, only. If two bands are supported, the two bands may be for different applications, e.g. lighting system operational communications and system element maintenance/commissioning. Alternatively, the two bands may support traffic segregation, e.g. one band may be allocated to communications of the entity owning/operating the system at the premises whereas the other band may be allocated to communications of a different entity such as the system manufacturer or a maintenance service bureau.

The MCU 830 may be a system on a chip. Alternatively, a system on a chip may include the transmitter 808 and receiver 810 as well as the circuitry of the MCU 830. As shown, the MCU 830 includes programming in the memory 822. A portion of the programming configures the CPU (processor) 823 to control light source and/or determine occupancy sensing/counting in an area in the lighting network, including the communications over one or more wireless communication. The programming in the memory 822 includes a real-time operating system (RTOS) and further includes a lighting application 827 which is firmware/software that engages in communications with controlling of the light source, for example, controlling the light source based on occupancy sensing/counting determined by the CPU 823. The lighting application 827 programming in the memory 822 carries out lighting control operations in the area. The programming for the determination of an occupancy and/or occupancy count in the area and/or lighting control may be implemented as part of the RTOS, as part of the lighting application 827, as a standalone application program, or as other instructions in the memory.

As shown by the above discussion, functions relating to configuring user preferences during configuration phase and utilizing the user preferences in the real-time operational phase to control the luminaire and building management appliances may be implemented on computers connected for data communication via the components of a wireless communication network, operating as one or more network connected hardware elements in the wireless communication network as shown in FIG. 6. Although special purpose devices may be used, such devices also may be implemented using one or more hardware platforms intended to represent a general class of data processing device, albeit with an appropriate network connection for data communication.

As known in the data processing and communications arts, a general-purpose computer typically comprises a central processor or other processing device, an internal communication bus, various types of memory or storage media (RAM, ROM, EEPROM, cache memory, disk drives etc.) for code and data storage, and one or more network interface cards or ports for communication purposes. The lighting control and building management control functionalities involve programming, including executable code of the software architecture, as well as associated stored data, e.g. the files or other data used or processed during execution of the software architecture. The software code is executable by the general-purpose computer that functions as an actual or physical gateway device and/or one or more general-purpose computers that implement the gateway functions in the cloud. In operation, the code is stored within the general-purpose computer platform. At other times, however, the software architecture and/or any associated files or other data may be stored at other locations and/or transported for loading into the appropriate general-purpose computer system. Execution of such code by a processor of the computer platform enables the platform to implement the methodology or functionalities for the implementation of configuring user preferences and utilizing the user preferences for controlling of the luminaire and the building management appliance, in essentially the manner performed in the implementations discussed and illustrated herein.

Figure 9:
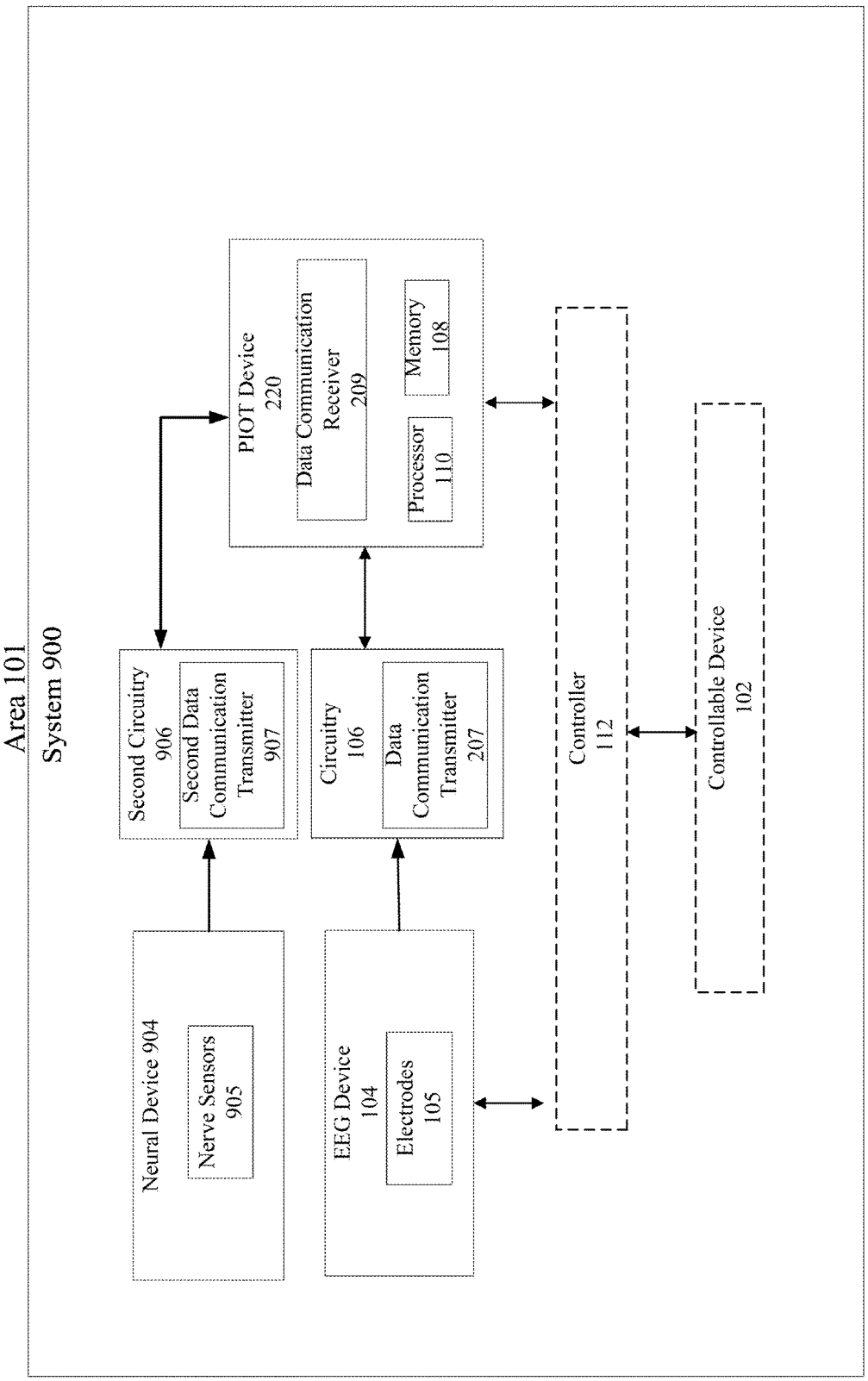
FIG. 9 illustrates another example of a system, in this case, for EEG based and neuro based control of a premises related service provided by a controllable device in an area of a premises.

FIG. 9 illustrates another example of a system 900, in this case, for EEG based and neuro based control of a premises related service provided by a controllable device in an area of a premises. The system 900 includes the same components as system 200 as described with respect to FIG. 2 and further includes a neural device 904 coupled to a second circuitry 906. In one example, the neural device 904 is configured to be positioned on some part of the human body, for example, as a glove to be worn on a person's hand or as a cuff to be worn on person's wrist or forearm. In another example, the neural device 904 is a neural sensor implanted inside the user's body. In one implementation, the neural device 904 includes one or more nerve sensors 905 configured to detect nerve signals from a nervous system of the part of the body such as finger, back, hand, forearm etc. on which the neural device 904 is positioned. In one implementation, as discussed above the memory 108 stores a data including a plurality of control instructions. In one example, a person may have neural device 904 positioned on the person's hand and an user input is a person moves his/her hand such that when the person moves his/her hand, the signals from the nerves of the person's hand are detected. In one example, the user ID is uniquely associated with the neural sensor device 904 identifying a user among a plurality of users of the neural device 904 in the premises 101. The user's location is tracked based on the user identification data associated with one or more of the EEG device 104, neural device 904 and the PIOT device 220.

In one implementation, as discussed above, the processor 110 generates, based on a control instruction among the plurality of instructions stored in the memory 108, a control data signal for control of an operation of a controllable device 102, which is configured to provide a premises related serve in the area 101. In one example, the second circuitry 906 processes the nerve signals received from the one or more nerve sensors 905 of the neural device. The second circuitry 906 also includes a second data communication transmitter 907, which functions to transmit the processed nerve signals to the PIOT device 220. In one implementation, the processor 110 processes the nerve signals similar to the processing of the signals detected by the electrodes 105 of the EEG device 104 as discussed with respect to FIG. 1.

In one implementation, the processor 110 is coupled to the circuitry 106 and thus during the configuration phase, configures the neural device 904 to receive data regarding the detected nerve signals and obtains a location identification associated with the first premises 101 at a time among a plurality of times; determines a control instruction from among a plurality of control instructions stored in the memory 108 associated with the detected nerve signals and stores the determined control instruction in association with the obtained location identification and the respective time, as a user preference data relative to the first premises 101 at the respective time, for communication to the controllable device 102.

In one implementation, during the real-time operational phase, the processor 110 utilizes the program instructions in the memory 108 to access the memory 108 to retrieve user preference data based on similarly detected nerve signals at a later time in the first premises 101, generates a control data signal associated with the control instruction such that the control data signal corresponds to a control operation among a plurality of control operations of the controllable device 102, and transmit the control data signal to the controller 112. In another implementation, during the real-time operational phase, the processor 110, access the memory 108 to retrieve a user preference data including a control instruction among a plurality of control instructions associated with a user ID of the neural device 904 at the first premises 101, determine that the detected nerve signals for the user ID do not correspond to the control instruction associated with the location ID relative to the first premises 101, analyze the detected nerve signals to determine that the detected nerve signals correspond to another control instruction among the plurality of control instructions stored in the memory 108 and updates the associated control instruction with other control instruction as the user preference data relative to the premises 101. In one implementation, generates another control data signal based on another control instruction.

Figure 10:
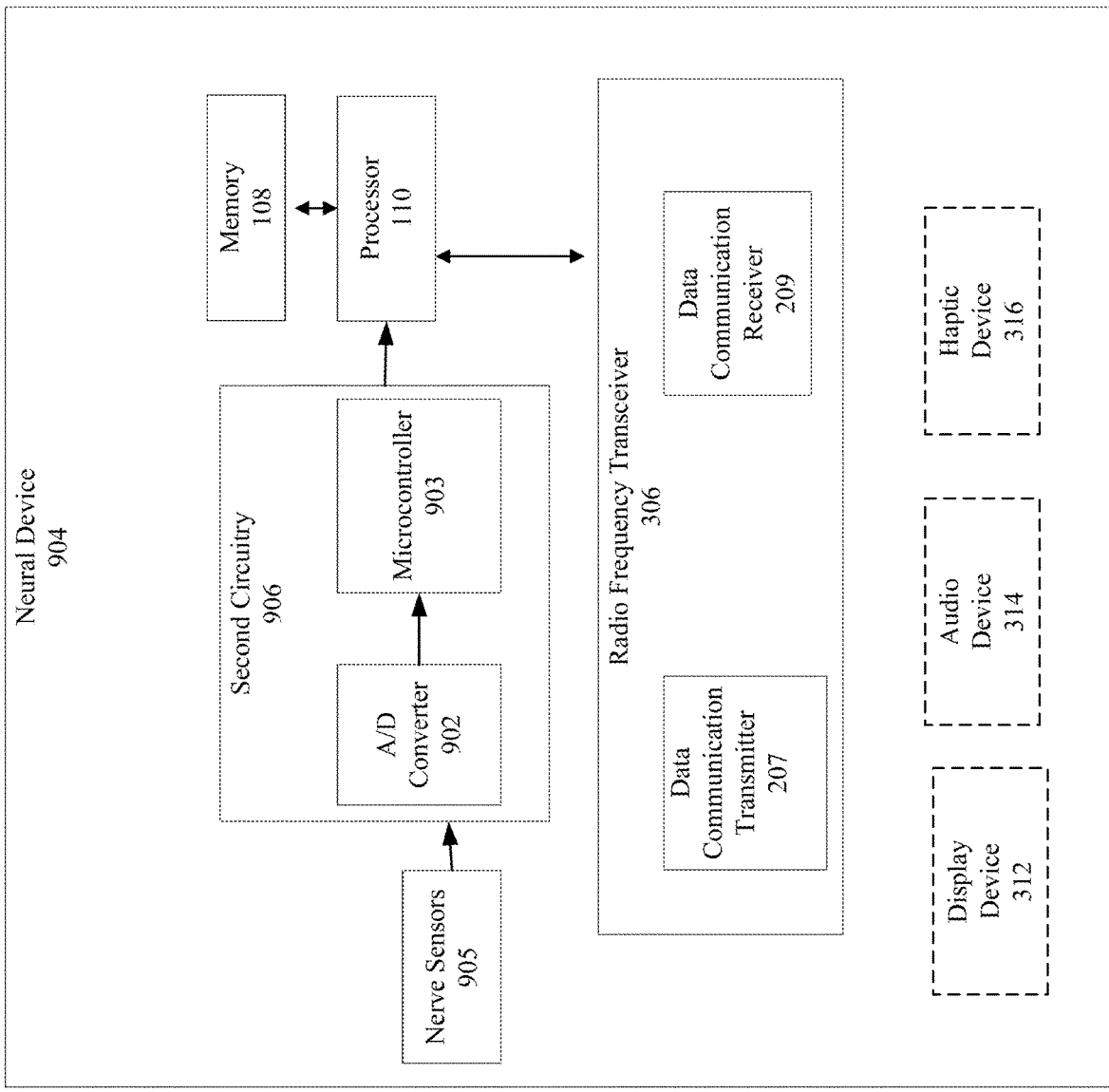
FIG. 10 is a functional block diagram of a neural device of FIG. 9.
Figure 11:
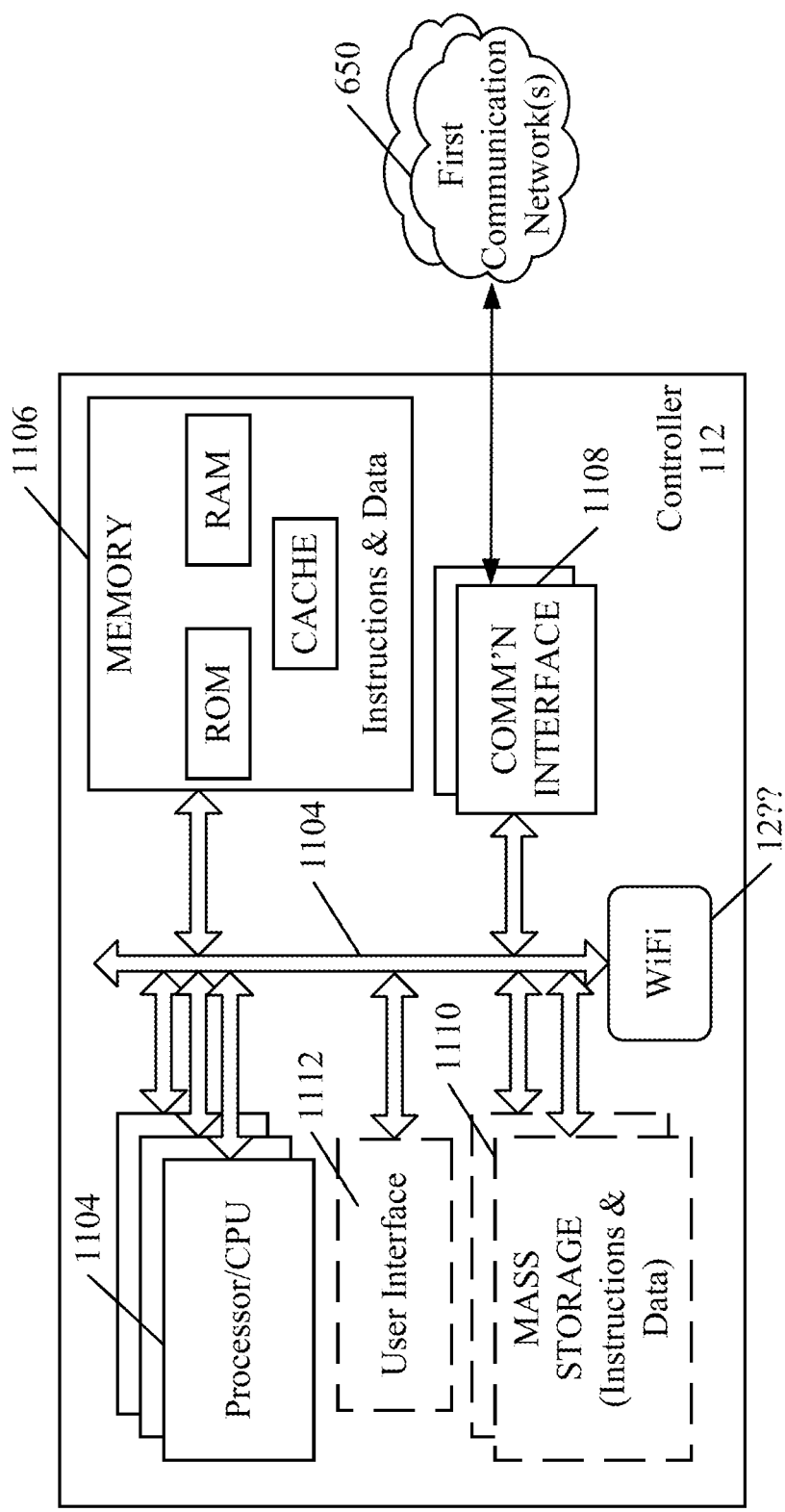
FIG. 11 is a functional block diagram of an example of a controller, e.g. for providing user hierarchy and utilizing the user hierarchy in an EEG based control of in an EEG based control of a premises related service.

FIG. 10 illustrates a functional block diagram of an example of the neural device 904 of FIG. 9. The neural device 904 includes the many components that are same as or similar to like-numbered components of the EEG device 104 as described with respect to FIG. 3 with the exception of the electrodes 105. Instead of EEG electrodes, the neural device 904 includes the nerve sensors 905. As shown, the second circuitry 906 includes an analog to digital (A/D) converter 902 and a microcontroller 903. Similar to the EEG device as discussed above, the second circuitry 906 of the neural device 904 processes the nerve signals detected by the nerve sensors 905. The signals detected by the nerve sensors 905 are analog signals. In one example, A/D converter 902 converts the analog signals into digital signals and the microcontroller 903 assembles the digital signals outputted from the A/D converter 902 into a format for a transmission to the processor 110. The processor 110 is coupled to the second circuitry 906 and thus configures the neural device 904 to receive the data regarding the detected nerve signals and processes the data, as discussed above with respect to FIG. 9, FIG. 11 illustrates a functional block diagram of an example of a controller, e.g. for providing user hierarchy and utilizing the user hierarchy in an EEG based control of in an EEG based control of a premises related service. As shown, the controller 112 includes a processor or other processing device 1102, an internal communication bus 1104, various types of memory or storage media (RAM, ROM, EEPROM, cache memory, disk drives etc.) such as memory 1106 for code and data storage, and one or more network interface cards or ports such as communication interface 1108 for communication with the first network communication 650. The controller 1112 may alternatively include a mass storage 1114 for storing instructions and data and a user interface 1116 both of which are coupled to the internal communication bus 1104.

In one implementation, the memory 1106 stores a plurality of different hierarchical classes or levels of user(s) as member(s), with each level having permissions to use one or more control instructions (corresponding to the one or more control operations of the controllable device 102) among the plurality of control instructions corresponding to the plurality of control operations of the controllable device 102. Some examples of levels of users include, building administrator, employee, guest etc. For example, the building administrator has permissions to all the control operations while the guest may only have permissions to one or two control operations. Specifically, the memory 1106 includes user IDs uniquely associated with a user device (e.g. EEG device 104, PIOT device 220, display device 312, audio device 314 or a haptic device 316) of the user identifying the user. In one implementation, the memory 1106 is accessible to the processor 1102.

In one implementation, the processor 1102 is in communication with a controllable device 112 (e.g. luminaire 602, BAC appliance 604. wall or floor switch/button or like controlling a number of the luminaires or a building management control system and other types of devices within the premises). In one implementation, the processor 1102 is coupled to or in communication with the data communication receiver 209 via the communication interface 1108. As discussed above, in one example, the data communication receiver 209 is a RF receiver configured to receive data over the RF spectrum.

In one implementation, the controller 112 receives user ID from the data communication transmitter 207 of the user device such as the EEG device 104 in FIG. 6 via the communication interface 1108. In another implementation, the controller 1102 receives the control data signal from the data communication transmitter 207 via the communication interface 1108. The data communication transmitter 207 is compatible with the data communication receiver. As discussed above, in one example, the data communication transmitter 207 is a RF receiver configured to transmit data over the RF spectrum. As discussed above, in one example, the processor 108 in the EEG device 104 generates a control data signal based on the detected EEG signals. As discussed above, the control data signal corresponds to a control operation among the plurality of control operations to control the controllable device 102. In one implementation, the processor 1102 accesses program instructions from the memory 1106 to perform various functions as described herein.

In one implementation, the processor 1102 receives the control data signal and the user ID via the data communication receiver 209. The processor 1102 access the memory 1106 to determine a privilege level of the hierarchy applicable to the user based on the received user ID. The processor 1102 controls the controllable device 102 based on the determined privilege level granting permission to utilize the corresponding control operation. Specifically, the processor 1102 determines whether the privilege level applicable to the user grants permission to utilize the control operation corresponding to the control data signal. In one implementation, upon the determination that the privilege level applicable to the user to grant permission to utilize the control operation corresponding to the control data signal, the processor 1102 implements a function so as to control the controllable device 102 to implement the corresponding control operation. In another implementation, upon the determination that the privilege level is not applicable to the user to grant permission to utilize the control operation corresponding to the control data signal, the processor 1102 blocks control of the controllable device 102 to implement the corresponding control operation. In one example, the processor 1102 generates a warning signal to the user of the user device, e.g. EEG device 104 via the user interface 1112. In another example, the processor 1102 provides a list of permitted one more control operations to the user device via the user interface 1112. In one example, the processor 1102 receives a selection of the permitted one or more control operations from the user of the user device. In one implementation, the user provides the selection through a user input via the user interface 1112. In one example, the user provides the user input similarly to the trusted input 111 as discussed above with respect to FIG. 1B. Upon receipt of a selection of the permitted one or more control operations, from the processor 1120 implements the function to control the controllable device 102 to implement the corresponding selected one or more control operations.

In one implementation, the controller 1102 receives another user ID and another control data signal from the data communication transmitter 207 of other EEG device 104', which is different from the EEG device 104 in FIG. 6D. As discussed above, other control data signal corresponds to another control operation among the plurality of control operations to control the controllable device 102. Other control operation is different from the control operation. In one implementation, the processor 1102 accesses program instructions from the memory 1106 to perform various functions as described herein.

In one implementation, the processor 1102 receives other control data signal and other user ID via the data communication receiver 209. The processor 1102 determines a privilege level of the stored hierarchy applicable to other user ID of another user of other EEG device 104'. As discussed above, the processor 1102 determines the privilege level of the stored hierarchy applicable to the user ID of user of the EEG device 104. The processor 1102 compares the privilege level of the user of the EEG device 104 with the privilege level of other user of the EEG device 104'. In one example, the processor 1102 determines that the privilege level of the user of the EEG device 104 is higher than the privilege level of other user of other EEG device 104'. Accordingly, the processor 1102 selects the control operation among the plurality of control operations to control the controllable device. In another example, the processor 1102 determines that the privilege level of other user of other EEG device 104' is higher than the privilege level of the user of the EEG device 104. Accordingly, the processor 1102 selects other control operation among the plurality of control operations to control the controllable device. In one example, the processor 1102 transmits the control operation or other control operation to the controller 102 via the first communication network 650.

Figure 12:
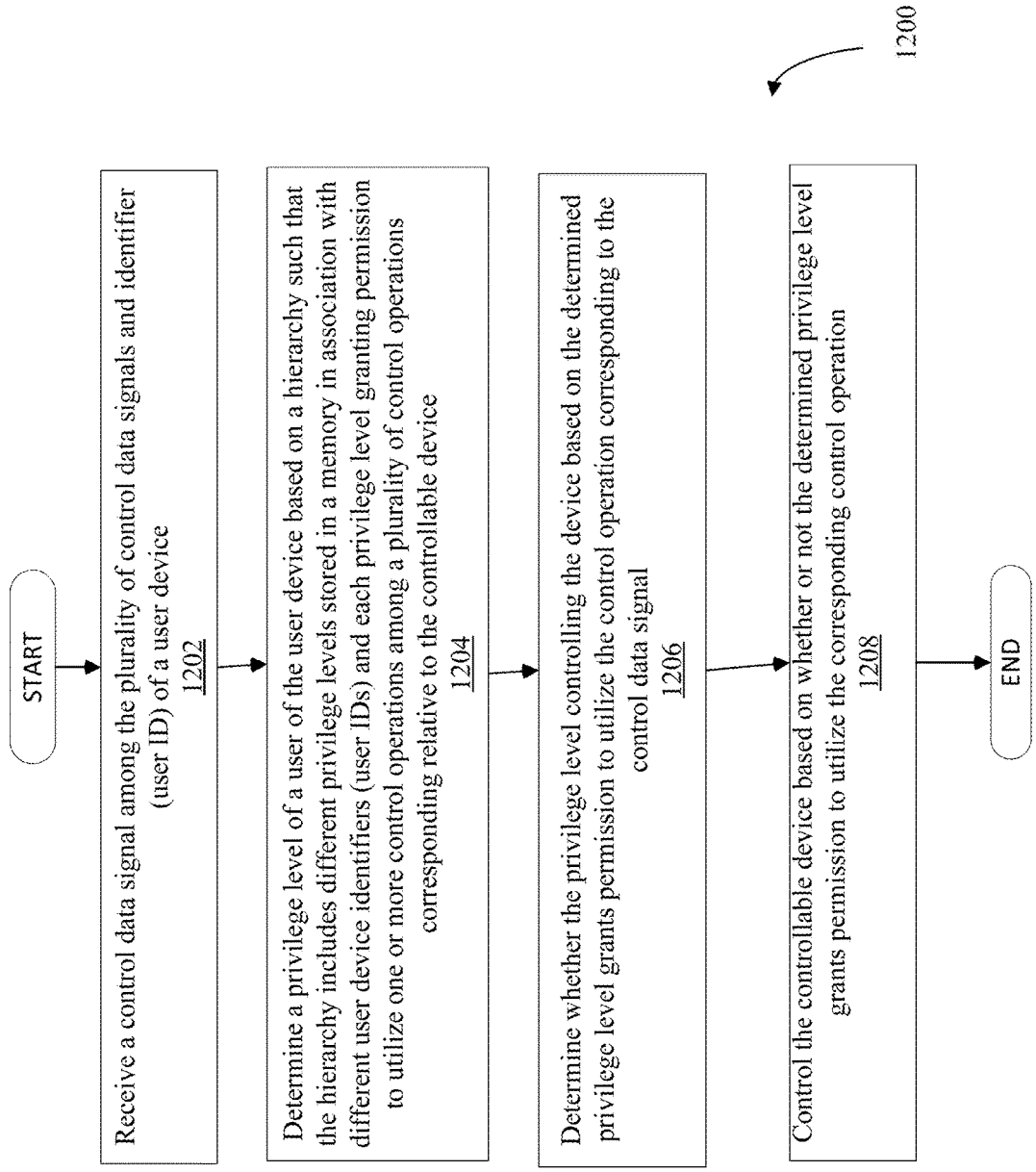
FIG. 12 is an example flowchart illustrating a method for providing user hierarchy and utilizing the user hierarchy in an EEG based system for controlling a premises related service provided by a controllable device in an area of a premises.

FIG. 12 is an example flowchart illustrating a method 1200 for providing user hierarchy and utilizing the user hierarchy in an EEG based system for controlling a premises related service provided by a controllable device in an area of a premises. In one implementation, the method 1200 is performed by the processor 1106 of FIG. 11 during the real-time operational phase.

At block 1202 receive a control data signal among the plurality of control data signals and identifier (user ID) of a user device. At block 1204, determine a privilege level of a user of the user device based on a hierarchy such that the hierarchy includes different privilege levels stored in a memory in association with different user device identifiers (user IDs) and each privilege level granting permission to utilize one or more control operations among a plurality of control operations corresponding relative to the controllable device. At block 1206, determine whether the privilege level controlling the device based on the determined privilege level grants permission to utilize the control operation corresponding to the control data signal. At block 1208, control the controllable device based on whether or not the determined privilege level grants permission to utilize the corresponding control operation.

At block 1204, access a memory to retrieve privilege level of a stored hierarchy applicable to a user of the user device based on the received user ID such that the stored hierarchy includes different privilege levels stored in a memory in association with different user IDs and each privilege level granting permission to utilize one or more control operations among a plurality of control operations relative to a device. In one example, the device is a controllable device. At block 1206, determine a privilege level of the user of the user device. At block 1208, control a device (e.g. controllable device) based on the determined privilege level that grants permission to utilize the control operation corresponding to the control data signal.

FIG. 12A is another example flowchart illustrating a method 1220 for providing user hierarchy and utilizing the user hierarchy in an EEG based system for controlling a premises related service provided by a controllable device in a premises among a plurality of premises. In one implementation, the method 1220 is performed by the processor 1106 of FIG. 11 during the real-time operational phase.

At block 1222 receive a control data signal among the plurality of control data signals and identifier (user ID) of a user device. At block 1224, determine a privilege level of a user of the user device based on a hierarchy, such that the hierarchy comprises different privilege levels stored in a memory in association with different user device identifiers (user IDs) and each privilege level granting permission to utilize one or more control operations among a plurality of control operations corresponding relative to the controllable device. At block 1226, a decision is made to determine whether the privilege level grants permission to utilize the control operation corresponding to the control data signal. When at block 1226, it is determined that the determined privilege level grants permission to utilize the control operation corresponding to the control data signal, then at block 1228, control the controllable device. When at block 1226, it is determined that the determined privilege level does not grant permission to utilize the control operation corresponding to the control data signal, then at block 1230, block control of the controllable device to implement the corresponding control operation. In one example, generate a warning signal to the user.

Figure 13:
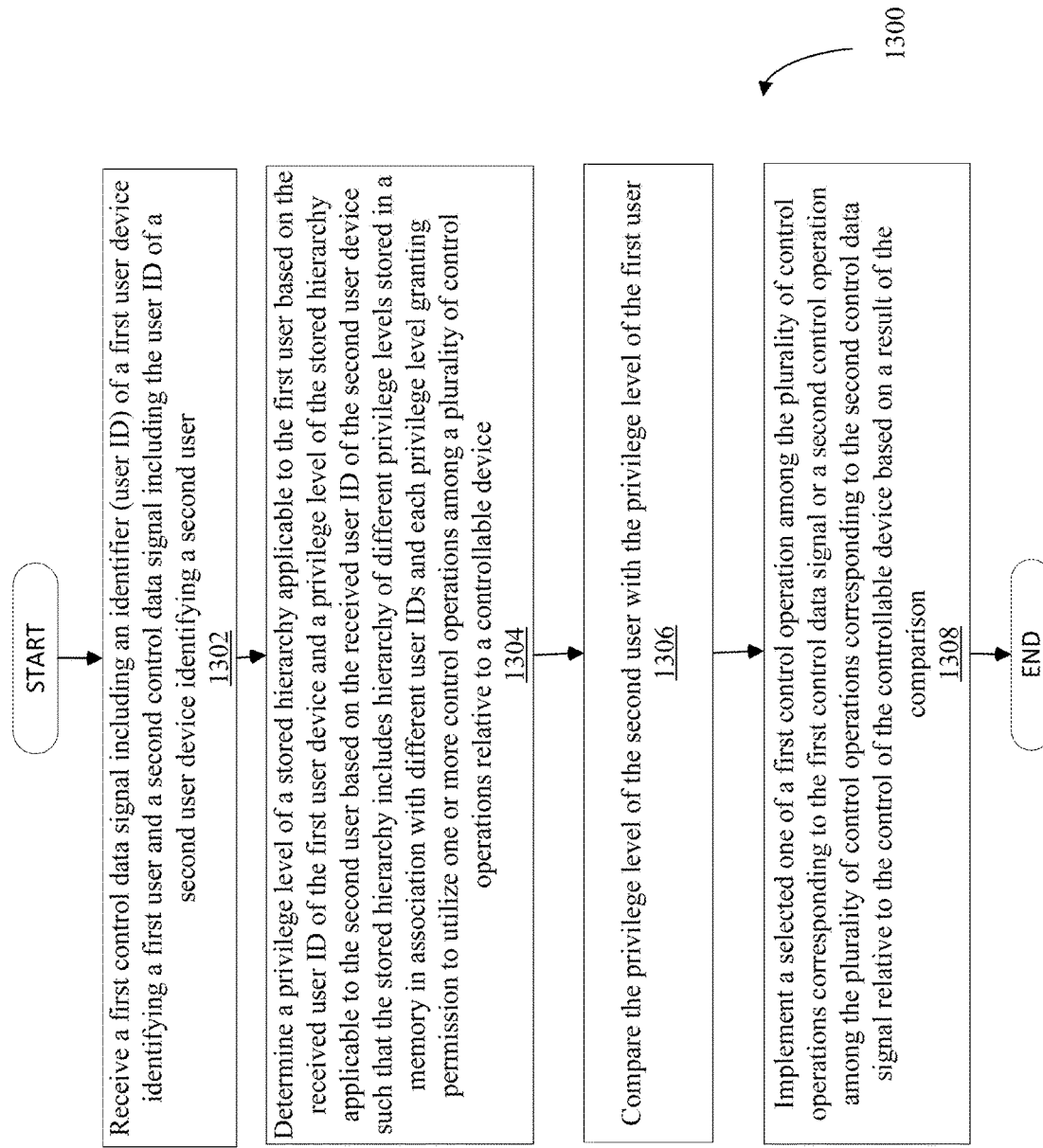
FIG. 13 is another example flowchart illustrating a method for providing user hierarchy and utilizing the user hierarchy in an EEG based system for controlling a premises related service provided by a controllable device in an area of a premises.

FIG. 13 is another example flowchart illustrating a method for providing user hierarchy and utilizing the user hierarchy in an EEG based system for controlling a premises related service provided by a controllable device in an area of a premises. In one implementation, the method 1300 is performed by the processor 1106 of FIG. 11 during the real-time operational phase.

At block 1302, receive a first control data signal including an identifier (user ID) of a first user device identifying a first user and a second control data signal including the user ID of a second user device identifying a second user. At block 1304, determine a privilege level of a stored hierarchy applicable to the first user based on the received user ID of the first user device and a privilege level of the stored hierarchy applicable to the second user based on the received user ID of the second user device such that the stored hierarchy includes hierarchy of different privilege levels stored in a memory in association with different user IDs and each privilege level granting permission to utilize one or more control operations among a plurality of control operations relative to a controllable device. At block 1306, compare the privilege level of the second user with the privilege level of the first user. At block 1308, implement a selected one of a first control operation among the plurality of control operations corresponding to the first control data signal or a second control operation among the plurality of control operations corresponding to the second control data signal relative to the control of the controllable device based on a result of the comparison.

Figure 15:
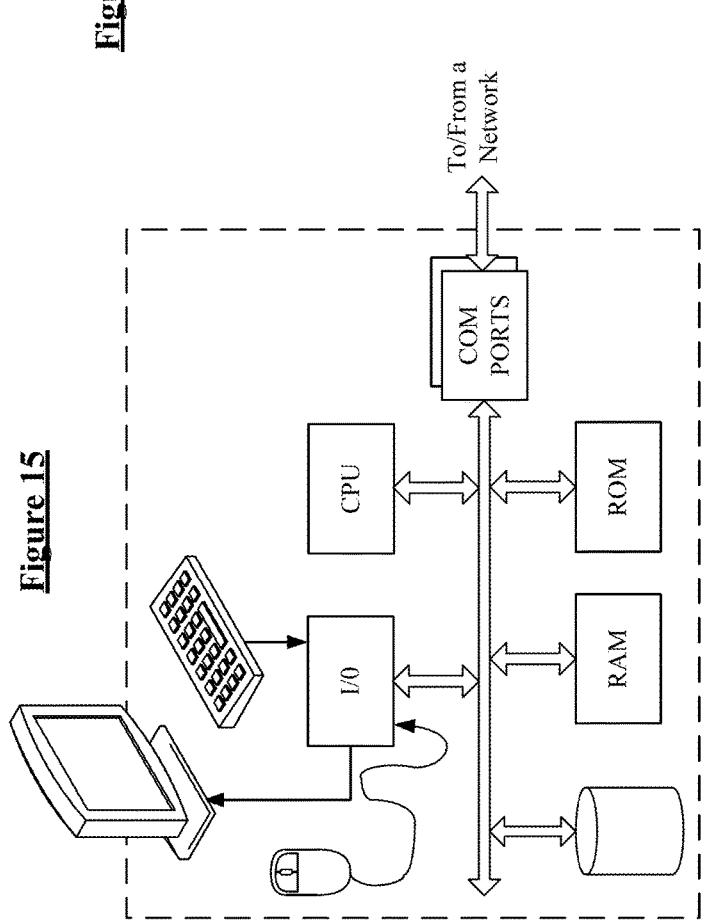
FIG. 15 is a simplified functional block diagram of a personal computer or other work station or terminal device, for possible communication with the gateway or cloud implementation of the control system.
Figure 14:
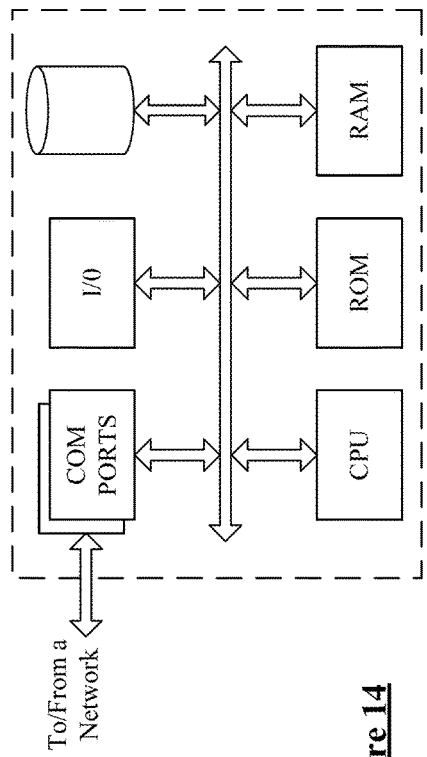
FIG. 14 is a simplified functional block diagram of a computer that may be configured as a host or server, for example, to function as the gateway or as an outside/cloud server on of the control system examples.

FIGS. 14 and 15 provide functional block diagram illustrations of general purpose computer hardware platforms. FIG. 14 illustrates a network or host computer platform, as may typically be used to implement a server, gateway or cloud computing platform. FIG. 15 depicts a computer with user interface elements, as may be used to implement a personal computer or other type of work station or terminal device, although the computer of FIG. 15 may also act as a server, gateway, host computer, etc. if appropriately programmed. It is believed that those skilled in the art are familiar with the structure, programming and general operation of such computer equipment and as a result the drawings should be self-explanatory.

A network computer, for example (FIG. 14), includes a data communication interface for packet data communication. That computer element also includes a central processing unit (CPU), in the form of one or more processors, for executing program instructions. The network computer platform typically includes an internal communication bus, program storage and data storage for various data files to be processed and/or communicated by the server or gateway functions, although the network computer element often receives programming and data via network communications. The hardware elements, operating systems and programming languages of such computers are conventional in nature, and it is presumed that those skilled in the art are adequately familiar therewith. Of course, the functions relating to the providing EEG user preference related configuration methodology and/or user access hierarchy in an EEG control based system, implemented via the software architecture, and may be implemented in a distributed fashion on a number of similar network computer hardware platforms, to distribute the processing load and/or offer the gateway functionalities as a cloud service.

Figure 16:
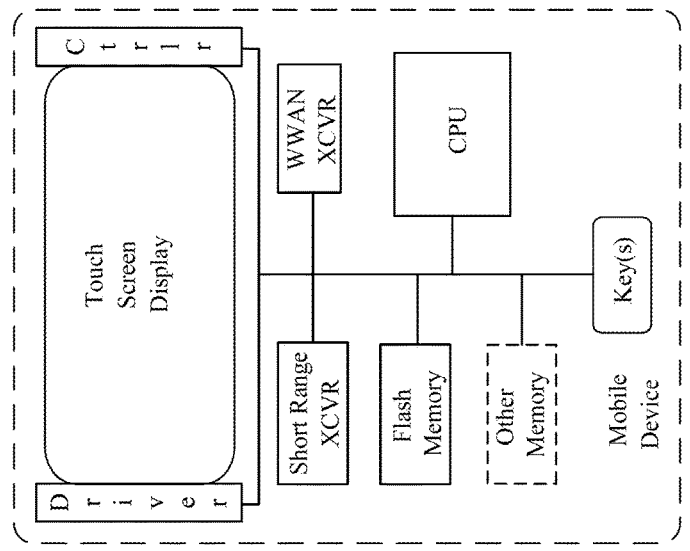
FIG. 16 is a simplified functional block diagram of a mobile device, e.g. smartphone or tablet, as an alternate example of a user terminal device, for possible communication with the gateway or cloud implementation of the control system.

A computer type user terminal device, such as a PC or tablet computer, similarly includes a data communication interface CPU, main memory and one or more mass storage devices for storing user data and the various executable programs (see FIG. 15). A mobile device type user terminal (FIG. 16) may include similar elements, but will typically use smaller components that also require less power, to facilitate implementation in a portable form factor. The various types of user terminal devices will also include various user input and output elements. A computer, for example, may include a keyboard and a cursor control/selection device such as a mouse, trackball, joystick or touchpad; and a display for visual outputs. A microphone and speaker enable audio input and output. Some smartphones include similar but smaller input and output elements. Tablets and other types of smartphones utilize touch sensitive display screens, instead of separate keyboard and cursor control elements. The hardware elements, operating systems and programming languages of such user terminal devices also are conventional in nature, and it is presumed that those skilled in the art are adequately familiar therewith.

In one implementation, the user input and any desired information output to the user (e.g. as to what command the system generates), during operational (only) phase might utilize a computer (see FIG. 15) or a mobile device (see FIG. 16) in communication with the PIOT device or the EEG device. Depending on processing power, the external computer or mobile device might make the determinations of appropriate associations of the detected EEG signals, tell the EEG device or the PIOT device to store in the memory, the recognition data characterizing the detected EEG signals and tell the EEG device or the PIOT device to update the characterizing data in the memory.

Hence, aspects of the functionalities for the configuration and real-time operation of EEG control based system as outlined above may be embodied in programming for the software architecture (see e.g. EEG device 104 of FIGS. 1, 2 and 3, and/or the PIOT device of FIGS. 2 and 4). Program aspects of the technology may be thought of as "products" or "articles of manufacture" typically in the form of executable code and/or associated data that is carried on or embodied in a type of machine readable medium. "Storage" type media include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer of a manufacturer or control service provider into the computing element that will run the software architecture. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Program instructions may comprise a software or firmware implementation encoded in any desired language. Programming instructions, when embodied in a machine readable medium accessible to a processor of a computer system or device, render a computer system or a device into a special-purpose machine that is customized to perform the operations specified in the program instructions.

Unless otherwise stated, any and all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

While the foregoing has described what are considered to be the best mode and/or other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present concepts.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

What is claimed is:

1. A system comprising:
  an electroencephalography (EEG) device configured to be positioned on a head of a user, wherein the EEG device includes one or more electrodes configured to detect EEG signals from the brain of the user;
  circuitry coupled to the one or more electrodes configured to process the EEG signals detected via the one or more electrodes of the EEG device;
  a processor coupled to or in communication with the circuitry;
  a memory accessible by the processor;
  program instructions stored in the memory for execution by the processor;
  wherein execution of the program instructions configures the processor to:
    in an configuration phase, for each respective location among a plurality of locations at a respective time among a plurality of times:
      obtain an identification (ID) associated with the respective premises at the respective time;
      determine a control instruction associated with the EEG signals detected via the one or more electrodes of the EEG device, from among a plurality of control instructions; and
      store the determined control instruction in association with the obtained premises ID, as a user preference data relative to the respective location; and
    at a later time, during an operational phase at the respective location, utilize the stored user preference data to:
      communicate a control data signal corresponding to the determined control instruction to a controllable device at the respective premises based at least in part on similar EEG signals detected at the later time via the one or more electrodes of the EEG device and reception of the premises ID at the respective premises.

2. The system of claim 1, wherein during the configuration phase, the processor is further configured to:
  store the determined control instruction as the user preference data relative to the respective time.

3. The system of claim 1, wherein during the operational phase, the execution of the program instructions further configures the processor to:
  upon detection of the similar EEG signals at the later time, access the memory to retrieve the user preference data associated for the user of the EEG device at the respective premises
  determine whether the control instruction corresponds to the later detected similar EEG signals;
  in response to the determination that the control instruction corresponds to the later detected similar EEG signals, generate a control data signal associated with the control instruction, wherein the control data signal corresponds to a control operation among a plurality of control operations of the controllable device; and
  transmit the control data signal to a controller of the controllable device, wherein the controller is configured to provide the control operation among the plurality of control operations of the controllable device in response to the control data signal.

4. The system of claim 1, wherein during the operational phase, the execution of the program instructions further configures the processor to:
  upon detection of the similar EEG signals at the later time, access the memory to retrieve the user preference data associated for the user of the EEG device at the respective premises;
  determine whether the control instruction corresponds to the later detected similar EEG signals;
  in response to the determination that the control instruction does not correspond to the later detected similar EEG signals, update the control instruction in the user preference data at the respective premises.

5. The system of claim 4, wherein to update, the processor determines another control instruction among the plurality of control instructions corresponding to the later detected similar EEG signals and replaces the control instruction with the another control instruction in the user preference data, wherein the another control instruction is different than the control instruction.

6. The system of claim 5, wherein during the operational phase, the execution of the program instructions further configures the processor to generate another control data signal associated with the another control instruction, wherein the another control data signal corresponds to another control operation among the plurality of control operations such that the another control data signal is different from the control data signal and the another control operation is different from the control operation.

7. The system of claim 3, wherein during the operational phase, the execution of the program instructions further configures the processor to:
update the associated control instruction in the user preference data at the respective premises based on an input provided by the user via a user device.

8. The system of claim 7, wherein during the operational phase, the execution of the program instructions further configures the processor to:
provide the user preference data at the respective premises to the user via a user device;
based upon the input from the user via the user device, determine another control instruction among the plurality of control instructions;
replace the control instruction with the another control instruction in the user preference data, wherein the another control instruction is different than the control instruction; and
generate another control signal associated with the another control instruction, wherein the another control data signal corresponds to another control operation among the plurality of control operations such that the another control data signal is different from the control data signal and the another control operation is different from the control operation.

9. The system of claim 1, wherein a user identification data is stored in the memory in association with the EEG device, for use in identifying the user of the EEG device among a plurality of potential users of the controllable device.

10. A system, comprising:
a first processor coupled to or in communication with a controllable device to selectively provide a premises related service in a premises;
a receiver coupled to the first processor;
a first memory, accessible to the first processor;
a hierarchy of different privilege levels stored in the first memory in association with different user device identifiers, each privilege level granting permission to utilize one or more control operations among a plurality of control operations relative to the controllable device; and
a user device comprising:
an electroencephalography (EEG) device configured to be positioned on a head of a user, wherein the EEG device includes one or more electrodes configured to detect EEG signals from the brain of the user;
circuitry coupled to the one or more electrodes configured to process the EEG signals detected via the one or more electrodes of the EEG device;
a transmitter compatible with the receiver;
a second processor coupled to the transmitter and coupled to or in communication with the circuitry; and
a second memory accessible by the processor storing an identifier of the user device and program instructions for the second processor, execution the program instructions configuring the second processor of the user device to:
generate a control data signal based on the detected EEG signals, wherein the control data signal corresponds to a control operation among a plurality of control operations to control the controllable device; and
transmit, via the transmitter, the control data signal and the identifier of the user device to the first processor,
wherein the first processor is configured to implement functions to:
receive the control data signal and the identifier of the user device via the receiver:
determine a privilege level of the stored hierarchy applicable to the user based on the received identifier of the user device; and
control the controllable device based on whether or not the determined privilege level grants permission to utilize the corresponding control operation.

11. The system of claim 10, wherein upon the determined privileged level granting permission to utilize the corresponding control operation, the first processor is configured to implement the function so as to, control the controllable device to implement the corresponding control operation.

12. The system of claim 10, wherein the first processor is configured to implement the function so as to, upon the determined privileged level not granting permission to utilize the corresponding control operation, the first processor is configured to implement the function so as to:
block control of the controllable device to implement the corresponding control operation; and
generate a warning signal to the user.

13. The system of claim 10, wherein the first processor is configured to:
provide a list of the permitted one or more control operations to the user device; and
upon receipt of a selection of the permitted one or more control operations from the user of the user device, implement the function so as to, control the controllable device to implement the corresponding selected one or more control operation.

14. A system comprising:
a processor coupled to or in communication with a controllable device to selectively provide a premises related service a premises;
a receiver coupled to the processor;
a memory accessible to the processor, wherein the memory stores a hierarchy of different privilege levels in association with different user device identifiers and each level having permission to one or more control operations among a plurality of control operations to control the controllable device;
a first user device, comprising:
a first electroencephalography (EEG) device configured to be positioned on a head of a first user, wherein the first EEG device includes one or more electrodes configured to detect EEG signals from the brain of a first user;
a first circuitry coupled to the one or more electrodes configured to process the EEG signals detected via the one or more electrodes of the first EEG device;
a first transmitter compatible with the receiver;

a first processor coupled to the first transmitter and coupled to or in communication with the first circuitry;

a first memory accessible by the first processor storing an identifier of the first user device and program instructions such that execution the program instructions configures the first processor of the first user device to:

generate a first control data signal based on the detected EEG signals; wherein the first control data signal corresponds to a first control operation among a plurality of control operations to control the controllable device; and transmit, via the transmitter, the first control data signal and the identifier of the first user device to the processor, a second user device, comprising:

a second electroencephalography (EEG) device configured to be positioned on a head of a second user, wherein the second EEG device includes one or more electrodes configured to detect EEG signals from the brain of a second user;

a second circuitry coupled to the one or more electrodes configured to process the EEG signals detected via the one or more electrodes of the second EEG device;

a second transmitter compatible with the receiver;

a second processor coupled to the second transmitter and coupled to or in communication with the second circuitry;

a second memory accessible by the second processor storing an identifier of the second user device and program instructions such that execution the program instructions configures the second processor of the second user device to:

generate a second control data signal based on the detected EEG signals; wherein the second control data signal corresponds to a second control operation among the plurality of control operations to control the device, wherein the second control operation is different from the control operation; and transmit, via the second transmitter, the second control data signal and the identifier of the second user device to the processor, wherein the processor is configured to access the memory to execute program instructions stored in the memory such that execution of the program instructions configures the processor to:

receive the first control data signal including the identifier of the first user device and the second control data signal including the identifier of the second user device via the receiver;

determine a privilege level of the stored hierarchy applicable to the first user based on the received identifier of the first user device and a privilege level of the stored hierarchy applicable to the second user based on the received identifier of the second user device;

compare the privilege level of the second user with the privilege level of the first user; and implement a selected one of the first control operation or the second control operation relative to the control of the controllable device based on a result of the comparison.

15. The system of claim 14, wherein to compare the processor to determine whether the privilege level of the first user is higher than the privilege level of the second user.

16. The system of claim 15, whereon upon the determination that the privilege level of the first user is higher than the privilege level of the second user, the processor to select the first control operation for implementation relative to the control of the controllable device.

17. The system of claim 15, wherein upon the determination that the privilege level of the first user is not higher than the privilege level of the second user, the processor to select the second control operation for implementation relative to the control of the controllable device.

* * * * *